United States Patent [19]

Robins et al.

[11] Patent Number: 5,026,836
[45] Date of Patent: Jun. 25, 1991

[54] 6-SULFENAMIDE, 6-SULFINAMIDE AND 6-SULFONAMIDE PURINES, PURINE NUCLEOSIDES, PURINE NUCLEOTIDES, PHARMACEUTICAL COMPOSITIONS, AND PROCESSES OF MAKING

[75] Inventors: Roland K. Robins; Ganapathi R. Revankar, both of Irvine; Naeem B. Hanna, Costa Mesa, all of Calif.

[73] Assignee: Nucleic Acid Research Institute, Costa Mesa, Calif.

[21] Appl. No.: 275,113

[22] Filed: Nov. 22, 1988

Related U.S. Application Data

[63] Continuation-in-part of Ser. No. 133,143, Dec. 14, 1987, abandoned.

[51] Int. Cl.$^5$ .................. C07H 19/14; C07H 19/167; C07H 19/173; C07H 19/20
[52] U.S. Cl. ........................ 536/24; 536/26; 536/27; 536/28
[58] Field of Search ....................... 536/23, 24, 26–29; 514/45–48

[56] References Cited

PUBLICATIONS

Fieser et al., Reagents for Organic Synthesis, vol. 2, p. 281, line 32, Wiley Interscience, New York, N.Y., 1969.
Fieser et al., Reagents for Organic Synthesis, vol. 3, Wiley-Interscience, New York, N.Y., 1972, see p. 50, line 10.
Fieser et al., Reagents for Organic Synthesis, vol. 5(a), Wiley-Interscience, New York, N.Y., 1975, p. 104, line 5.
Fieser et al., Reagents for Organic Synthesis, vol. 5(b), Wiley-Interscience, New York, N.Y., 1975, see p. 33, line 12, p. 127, line 10.
Fieser et al., Reagents for Organic Synthesis, vol. 7, Wiley-Interscience, New York, N.Y., 1983, see p. 58, line 9.
Fieser et al., Reagents for Organic Synthesis, vol. 8(a), Wiley-Interscience, New York, N.Y., 1980, see p. 2, lines 9–10.
Fieser et al., Reagents for Organic Synthesis, vol. 8(b), Wiley-Interscience, New York, N.Y., 1983, see p. 44, lines 1–2.
March, J., Advanced Organic Chemistry, Reactions, Mechanism & Structure, McGraw-Hill Book Co., New York, N.Y., 1968 see p. 887, sec. 9–28.
Paterson et al., Chemical Abstracts, vol. 88:58916m, 1978.
Paterson et al., Chemical Abstracts, vol. 88:45687n, 1978.
Synthesis and in Vivo Antitumor Activity of 2-Amino-9-H-Purine-6-Sulfenamide, -Sulfinamide, and -Sulfonamide and Related Purine Ribonucleosides, Revanker, et al., J. Medicinal Chemistry, 1990, 33, 121.
Oxidation of 2-Amino-9- -D-Ribofurnosyl-purine-6-Sulfenamide to the Corresponding 6-Sulfonamide Facilitates Changes in Biologic Characterization that include Activity Against Thiopurine-Refractory Experimental Leudemia, Finch et al., Cancer Letters, 50(1990), 63–70.
Chemotherapeutic Characterization in Mice of 2-Amino-9- -D-Ribofuranosylpurine-6-Sulfinamide (Sulfinosine), A Novel Purine Nucleoside with Unique Antitumor Properties, Avery et al., Cancer Research 50, 2625, May 1, 1990.

Primary Examiner—Johnnie R. Brown
Assistant Examiner—L. Eric Crane
Attorney, Agent, or Firm—Herb Boswell

[57] ABSTRACT

6-Sulfenamide, 6-sulfinamide and 6-sulfonamide purines, purine nucleosides, purine nucleotides and 3 and 7 deaza and 8 aza derivatives thereof of structure:

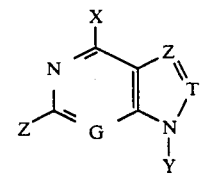

wherein
Z is H or —NH$_2$;
X is —S—NH$_2$, (Abstract continued on next page.)

1-A

1-B

1-C

1-D

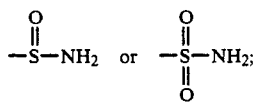

T is C—H, G is N and Q is N; or
T is C—H, G is N and Q is C—H; or
T is N, G is N and Q is C—H; or
T is C—H, G is C—H and Q is N;
Y is H or an α-pentofuranose or β-pentofuranose of the formula:

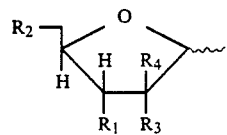

wherein
$R_1$ and $R_2$ independently are H, OH, —O-acyl or

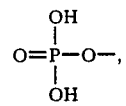

or together $R_1$ and $R_2$ are

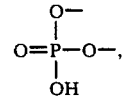

and $R_3$ and $R_4$ are H or one of $R_3$ or $R_4$ is OH and the other is H; provided that when Y is H, Z is —$NH_2$; and acceptable salt thereof are prepared and are useful as antitumor agents or they are intermediates for compounds which are antitumor agents. The compounds are used to treat an affected warm blooded host by serving as the active ingredients of suitable pharmaceutical compositions.

28 Claims, 1 Drawing Sheet

6-SULFENAMIDE, 6-SULFINAMIDE AND 6-SULFONAMIDE PURINES, PURINE NUCLEOSIDES, PURINE NUCLEOTIDES, PHARMACEUTICAL COMPOSITIONS, AND PROCESSES OF MAKING

CROSS REFERENCE TO RELATED APPLICATIONS

This application is a continuation in part of our prior application serial number 133,143, filed Dec. 14, 1987, now abandoned in the names of Roland K. Robins, Ganapathi R. Revankar and Naeem B. Hanna, entitled Antitumor 6-Sulfenamide, 6-Sulfinamide and 6-Sulfonamide Purines, Purine Nucleosides, Purine Nucleotides And Related Compounds, and assigned to the same assignee as this application, the entire disclosure of which is herein incorporated by reference.

BACKGROUND OF INVENTION

This invention is directed to certain 6-sulfenamide, 6-sulfinamide, and 6-sulfonamide purines, purine nucleosides and purine nucleotides including 3-deaza, 7-deaza and 8-aza derivatives thereof, to their preparation and to using these compounds to treat malignant tumors in vivo.

Certain antimetabolites are known useful cancer chemotherapeutic agents. One such antimetabolite chemotherapeutic agent is 6-mercaptopurine. 6-Mercaptopurine was initially found to be highly active against adenocarcinoma and currently 6-mercaptopurine is utilized as a drug of choice in the treatment of leukemia. Its use in the treatment of leukemia led to dramatic increases in controlling this disease. Other useful antimetabolites are 6-thioguanine and 5-bromouracil. Nucleoside and nucleotide analogs of these and other purines and pyrimidines had been synthesized and tested as antitumor agents.

Purine and pyrimidine nucleosides and nucleotides are ubiquitous throughout biological systems. It further appears that most of the analogs of purines and pyrimidines exert their biological activity only after conversion to a corresponding nucleotide. In view of this, a number of purine and pyrimidine nucleosides and nucleotides have been synthesized and screened for their antitumor properties.

To be an effective chemotherapeutic agent a compound must possess a number of desirable properties. First of all, it must, of course, be an active antitumor agent. Coupled with this, it must not exhibit too great a host toxicity or must exhibit reversible toxicity such that the host is capable of surviving the chemotherapeutic treatment regimen. Optimally the chemotherapeutic agent should not induce the development of drug resistant cell lines. The inducement of drug resistant cell line occurs with certain known chemotherapeutic agents, as for instance, 6-mercaptopurine and cytosine arabinoside.

Further, effective chemotherapeutic agents need to transport to the site in the body inflicted with the neoplastic condition. Thus depending upon the type of tumor, this requires that chemotherapeutic agents be capable of reaching tumor containing organs. This includes being able to effectively penetrate the central nervous system by crossing the blood brain barrier. As is evident by the sparsity of clinically effective chemotherapeutic agents, very few compounds possess a sufficient number of these capabilities to be clinically useful.

Many effective chemotherapeutic agents require repeated dosing in order to progressively diminish and kill the neoplastic cell populations affecting the host. During these repeated administrations of the chemotherapeutic agent it is further advantageous for the agent to not develop resistant cell lines. Because of the development of resistant cells by certain drugs presently used in the treatment of many neoplastic disease states, combinations of drugs are usually utilized. Thus, as resistant cells develop to a first drug, treatment with a second or further drug is often made in an attempt to effectively treat the drug resistant neoplastic cells.

We have found that certain 6-sulfenamide, 6-sulfinamide and 6-sulfonamide purines, purine nucleosides and purine nucleotides and related analogs exhibit one or more of the properties discussed above, and further exhibit significant antitumor activity so as to be useful as antitumor agents in vivo.

SUMMARY OF THE INVENTION

The present invention relates to a novel class of 6-sulfenamide, 6-sulfinamide and 6-sulfonamide purines, purine nucleosides, purine nucleotides and 3 and 7 deaza and 8 aza derivatives thereof and to their preparation and use as antitumor agents.

In accordance with the invention, disclosed are compounds of the formula:

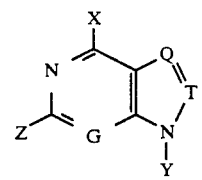

wherein
Z is H or —NH$_2$;
X is —S—NH$_2$,

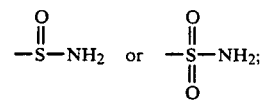

G, T and Q are C—H or N;
Y is H or an α-pentofuranose or β-pentofuranose of the formula:

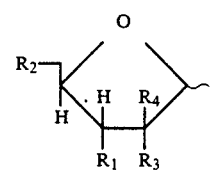

wherein
R$_1$ and R$_2$ independently are H, OH, —O—acyl or

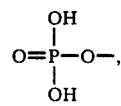

or together R$_1$ and R$_2$ are

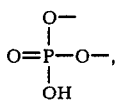

and $R_3$ and $R_4$ are H or one of $R_3$ or $R_4$ is OH and the other is H; provided that when Y is H, Z is $-NH_2$; and pharmaceutically acceptable salts thereof.

These compounds are useful as antitumor agents or they are intermediates for compounds which have these properties. They can be used to treat an affected host as, for example a mammalian host (i.e. a warm blooded host) by serving as the active ingredients of suitable pharmaceutical compositions.

Additionally, in accordance to the invention, an antitumor composition for the treatment of tumors in vivo contains as its active ingredient a therapeutic effective amount of a compound of the above formula.

Further, in accordance with the invention, tumors in warm blooded animals are treated by administering to the animal in need thereof, a pharmaceutical composition containing as the active component therein a therapeutically effect amount of a compound of the above formula.

The method of the invention and the antitumor composition of the invention used therein, are effective in bringing about regression, palliation, inhibition of growth, and remission of tumors.

Particularly useful are compound of the above formula wherein Y is a $\beta$-pentofuranose of the formula:

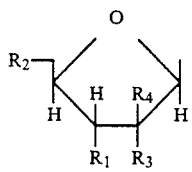

Included in this group are 2-amino-9-$\beta$-D-ribofuranosyl-9H-purine-6-sulfenamide (see compound 18), 2-amino-9-$\beta$-D-ribofuranosyl-9H-purine-6-sulfinamide (see compound 19), 2-amino-9-$\beta$-D-ribofuranosyl-9H-purine-6-sulfonamide (see compound 20) and 2-amino-9-(2-deoxy-$\beta$-D-erythro-pentofuranosyl)-9H-purine-6-sulfinamide (see compound 23).

Exhibiting particularly useful antitumor properties is the above 2-amino-9-$\beta$-D-ribofuranosyl-9H-purine-6-sulfinamide. This compound exhibits a particularly useful combination of solubility, activity and the lack of generating resistant cell lines as well as being able to penetrate the central nervous system and be active in both an oral and an injectable form.

For use in pharmaceutical compositions of the invention, a pharmaceutical carrier would be utilized. Preferably, the pharmaceutical carrier would be chosen to allow for administration of a suitable concentration of the active compounds of the invention either by oral administration, ophthalmic administration, topical administration, suppository administration or by suitable injection as a solution or suspension into the effected host. The dose and choice of administration of the active compounds of the invention would depend upon the host harboring the malignant tumor, the type of tumor, and the tumor site. For injection, the active compounds of the invention could be administered intravenously, intramuscularly, intracerebrally, subcutaneously, or intraperitoneally.

The compounds of the invention are especially useful in treating carcinomas, sarcomas and leukemias. Included in such a class are mammary, colon, bladder, lung, prostate, stomach and pancreas carcinomas and lymphoblastic and myeloid leukemias.

Other compounds of the invention are useful as intermediates for the preparation of the active antitumor compounds of the invention. Further certain of the compounds of the invention are useful as prodrugs for other active antitumor compounds of the invention.

DETAILED DESCRIPTION OF THE INVENTION

Figure 1:
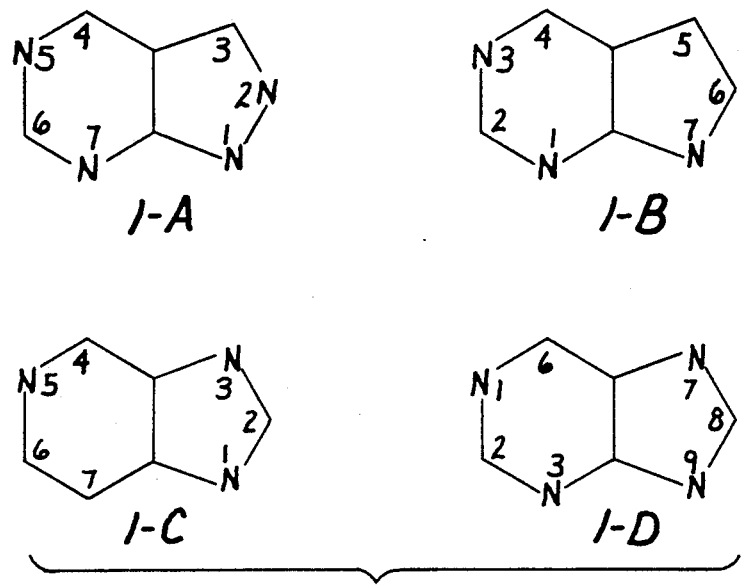
FIG. 1 is chemical structural illustration of the heterocycle ring structures and positional numbering of a pyrazolo[3,4-d]pyrimidine ring in FIG. 1-A, a pyrrolo[2,3-d]pyrimidine ring in FIG. 1-B, a imidazo[4,5-c]pyridine ring in FIG. 1-C and purine ring, i.e. imidazo[4,5-d]pyrimidine ring, in FIG. 1-D utilized for ring identification of compounds of the invention.
Figure 2:
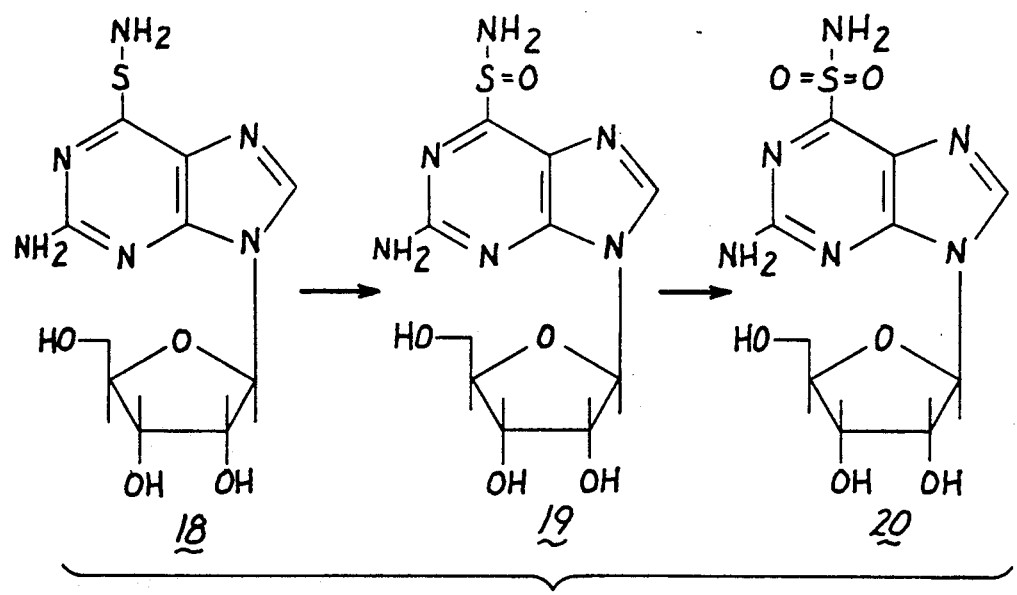
FIG. 2 is a chemical structural flowchart of representational compounds 18, 19 and 20 of the invention.

A group of 6-sulfenamide, 6-sulfinamide and 6-sulfonamide purines, purine nucleosides and purine nucleotides and related analogs have been found to have antitumor properties or be intermediates for compounds having such antitumor properties. Included in this group of compounds are purines which have been substituted on the purine ring at the 2 position with an amino group and various nucleosides and nucleotides as well as modification of the purine ring at the 3, 7, and 8 positions forming deaza and aza purines. Included in this group are the ribofuranosyl, the deoxyribofuranosyl and the arabinofuranosyl nucleosides, the monophosphates of these nucleosides and the 3′,5′-cyclic phosphates of these nucleosides and derivatives thereof. Included in the deaza and aza purine compounds are the 3-deaza and the 7-deaza purine as well as the 8-aza-7-deaza purine.

One particular compound, 2-amino-9-$\beta$-D-ribofuranosyl-9H-purine-6-sulfinamide, has exhibited good in vivo activity coupled with an excellent dose response performance while penetrating the central nervous system and exhibiting a lack of resistance cell generation. This compound is water soluble and orally active. Further, it has demonstrated activity against cells which have become resistant to other chemotherapeutic agents.

The 6-sulfonamide analog of this compound exhibits many of the properties of the 6-sulfinamide with the exception of lack of oral activity and CNS penetration. The deoxy derivative of this compound, i.e. the 2-deoxy-$\beta$-D-erythropentofuranosyl derivative, also exhibits good activity with increased water solubility.

While we do not wish to be bound by theory, it is believed that many purines, pyrimidines, and purine and pyrimidine nucleosides exhibit their antitumor activity by being enzymatically phosphorylated in situ to their 5′ phosphate derivative. Other enzyme systems are known which convert the 5′-phosphate to a 3′,5′-cyclic phosphate. Additionally, esterases are known which cleave phosphates and/or cyclic phosphates. In any event, activity has been shown for compounds of the invention as both nucleosides and nucleotides.

In addition to phosphate or cyclic phosphate derivatives (phosphoryl ester prodrugs) the compounds of the inventions can also be administered as acyl ester prodrugs which are then also cleaved in vivo to the parent compound. Suitable acyl derivatives can be selected as, for example, from formyl, acetyl, propionyl, butyryl, isobutyryl, hexanoyl and benzoyl. Preferably acetyl is utilized. One or more hydroxyl group on the nucleosides of the invention can be suitable reacted to yield such a $C_1$–$C_8$ acyl prodrug.

In performing the invention, a compound of the invention or a selected derivative thereof, is appropriately admixed with a suitable pharmaceutical carrier which may be as simple as sterilized water or could be a complex carrier having appropriate agents to suitably mimic certain biological environmental, i.e., pH or salt adjustment for solution suitable for intravenous, intramuscular or other injections, or other appropriate carrier manipulation for different routes of administration of the compounds of the invention.

In selecting a suitable pharmaceutical carrier, consideration of the type of tumor, the site of the tumor and the health and age of the host would be given. Additionally, if a derivatized form of a compound of the invention is used, consideration of the chemical reactivity of the derivative would also be given. Thus, if a phosphate form of a compound of the invention is used in practicing the invention, it might be used in the presence of a suitable buffer or an acceptable pharmaceutical salt thereof.

Acceptable salts of the phosphate moiety can be selected from, but not necessarily limited to the group consisting of alkali and alkaline earths, e.g. sodium, potassium, calcium, magnesium, lithium, or ammonium and substituted ammonium, trialklyammonium, dialkylammonium, alklyammonium, e.g. triethylammonium, trimethylammonium, diethylammonium, octylammonium, cetyltrimethylammonium and cetylpyridium.

Since the compounds of the invention are water soluble they could suitably be given to a host as a solution in a suitable carrier. Alternately, however, suspensions, emulsions, or other formulations of the compounds of the invention could be used where indicated. The pharmaceutical carrier, in addition to having a solubilizing or suspending agent therein, might include suitable diluents, buffers, surface active agents or other similar agents as are typically used in pharmaceutical carriers. However, the total composition of the pharmaceutical carrier would be chosen to be compatible with the site of the delivery, the mode of delivery, the concentration of the active ingredient and other parameters as are standard in the pharmaceutical arts.

The compounds of the invention would be suitably admixed with the pharmaceutical carrier such that they would be present in a composition of at least 0.1 percent by weight of the total composition. Preferably, the compounds of the invention would be present in a pharmaceutical carrier at a concentration of about 10% to about 90% by weight of the total composition.

A therapeutic effective amount of the compounds of the invention, as will be evident from the biological responses and solubilities given below, would be utilized in treating an affected host animal taking into consideration certain parameters such as the type of tumor, the tumor site, the form of administration of the compound, and the physical size and condition of the host. In any event, the actual amount should be sufficient to provide a chemotherapeutically effective amount of the agent in the host in a convenient carrier. This will be readily within the ability of those skilled in the Art given the disclosure herein.

The compounds of the invention can be given as single doses or as multiple doses divided into sub-doses given daily or over a period of days. As will be evident from the examples below, compounds of the invention exhibit certain dose response curves and, as such, optimization of a dosage schedule is well within the skill of the Art given the disclosure herein.

In novel processes of the invention, generally 6mercaptopurine derivatives as the purine base, nucleoside or nucleotide are treated with chloramine to prepare the corresponding 6-sulfenamides. The chloramine can be prepared in situ by reacting ammonium hydroxide with sodium hypochlorite. The 6-sulfenamides are then selectively oxidized either to the 6-sulfinamide or fully oxidized to the 6-sulfonamide compounds. Generally for selective oxidation to the 6-sulfinamide, 1 eq. of an oxidizing agent is utilized. For full oxidation to the 6-sulfonamide, further equivalents of the oxidizing agent are utilized. Preferred as an oxidizing agent for process of the invention is m-chloroperoxybenzoic acid.

The above processes have been found useful for both preparing free purines, purine nucleosides and purine nucleotides of the invention. Typically, the 6-sulfinamide is prepared utilizing 1 eq. of the above referred to m-chloroperoxybenzoic acid, and the 6-sulfonamide is prepared utilizing 4 eq. of m-chloroperoxybenzoic acid. It is evident that 6-sulfonamide compounds can be prepared directly from the corresponding 6-sulfenamide compounds or could be prepared via the 6-sulfinamide compounds as an intermediate.

Schemes I and II illustrate the general reaction schemes for preparation of compounds of the invention from starting 6-mercaptopurine precursors. In scheme I, the heterocycle utilized is a purine, whereas in scheme II various deaza and aza heterocycles are depicted. In cross reference between the schemes and the illustrative examples which follow, the numbers in the parentheses following the names that appear after each example refer to the compound numbers and structures that appear in schemes I and II.

SCHEME I

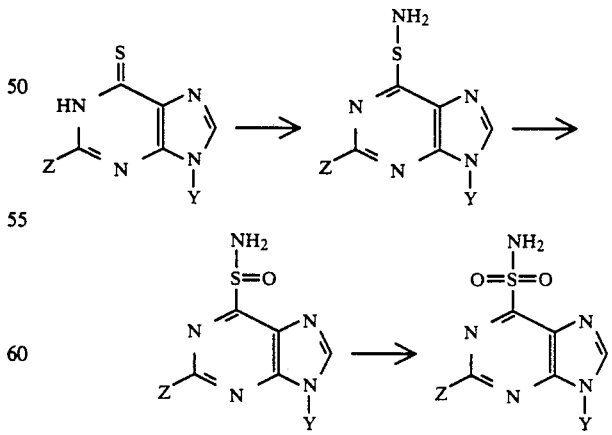

Z = —NH$_2$
Y = —H

COMPOUND 1 ⟶ COMPOUND 2 ⟶

-continued
SCHEME I

COMPOUND 3 → COMPOUND 4

Z = —H
Y = -β-D-ribofuranosyl
COMPOUND 5 → COMPOUND 6 →
COMPOUND 7 → COMPOUND 8

Z = —H
Y = -β-D-arabinofuranosyl
COMPOUND 9 → COMPOUND 10 →
COMPOUND 11 → COMPOUND 12

Z = —H
Y = -2-deoxy-β-D-erythro-pentofuranosyl
COMPOUND 13 → COMPOUND 14 →
COMPOUND 15 → COMPOUND 16

Z = —NH$_2$
Y = -β-D-ribofuranosyl
COMPOUND 17 → COMPOUND 18 →
COMPOUND 19 → COMPOUND 20

Z = —NH$_2$
Y = -2-deoxy-β-D-erythro-pentofuranosyl
COMPOUND 21 → COMPOUND 22 →
COMPOUND 23 → COMPOUND 24

Z = —NH$_2$
Y = -β-D-ribofuranosyl 5'-phosphate
COMPOUND 25 → COMPOUND 26 → COMPOUND 27

Z = —NH$_2$
Y = -β-D-ribofuranosyl 3',5'-cyclic phosphate
COMPOUND 28 → COMPOUND 29 → COMPOUND 30

Z = —NH$_2$
Y = -5-deoxy-β-D-ribofuranosyl
COMPOUND 40 → COMPOUND 41 →
COMPOUND 42 → COMPOUND 43

Z = —NH$_2$
Y = -2-deoxy-α-D-erythro-pentofuranosyl
COMPOUND 44 → COMPOUND 45 →

-continued
SCHEME I

COMPOUND 46 → COMPOUND 47

Z = —NH$_2$
Y = -β-D-arabinofuranosyl
COMPOUND 48 → COMPOUND 49 →
COMPOUND 50 → COMPOUND 51

Z = NH$_2$
Y = 2,3,5-tri-O-acetyl-β-D-ribofuranosyl
19
|
COMPOUND 58

SCHEME II

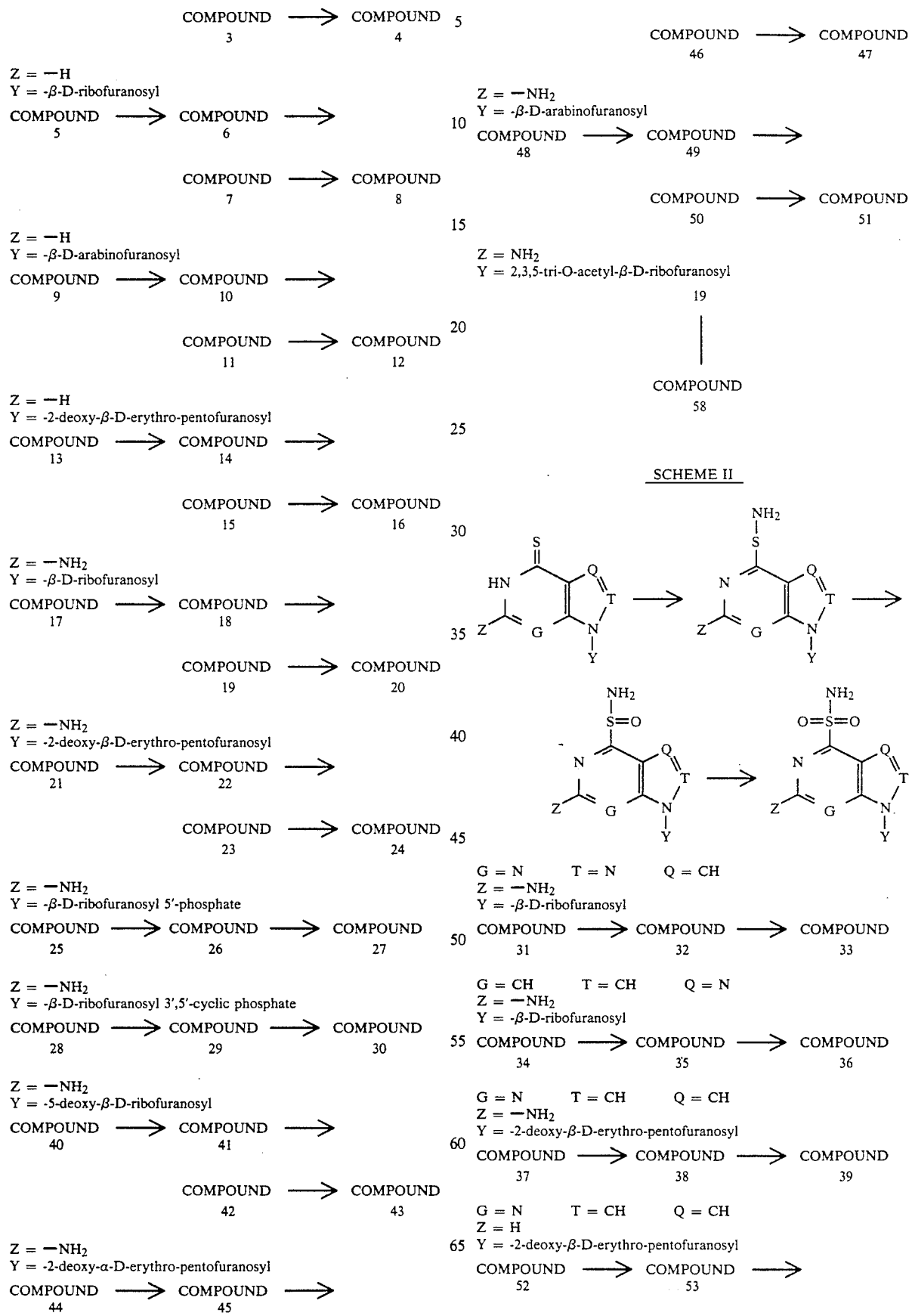

G = N    T = N    Q = CH
Z = —NH$_2$
Y = -β-D-ribofuranosyl
COMPOUND 31 → COMPOUND 32 → COMPOUND 33

G = CH    T = CH    Q = N
Z = —NH$_2$
Y = -β-D-ribofuranosyl
COMPOUND 34 → COMPOUND 35 → COMPOUND 36

G = N    T = CH    Q = CH
Z = —NH$_2$
Y = -2-deoxy-β-D-erythro-pentofuranosyl
COMPOUND 37 → COMPOUND 38 → COMPOUND 39

G = N    T = CH    Q = CH
Z = H
Y = -2-deoxy-β-D-erythro-pentofuranosyl
COMPOUND 52 → COMPOUND 53 →

-continued
SCHEME II

COMPOUND 54 ⟶ COMPOUND 55

G = N  T = N  Q = CH
Z = H
Y = -β-D-ribofuranosyl

COMPOUND 56 ⟶ COMPOUND 57 ⟶

The following illustrative examples are given for the preparation of compounds of the invention. Unless otherwise indicated, the various starting 6-mercaptopurine compounds or other compounds utilized for the starting materials were obtained from suitable commercial sources. In these illustrative examples, the preparation of the compounds of the invention is accomplished utilizing the processes of the invention.

EXAMPLE 1

2-Aminopurine-6-sulfenamide (2)

To an ice-cold 5.25% sodium hypochlorite solution (33.8 mL) was added 7N NH$_4$OH (17.8 mL) and stirred for 10 minutes. A solution of 2-aminopurine-6-thione 1, see A. G. Beaman and R. K. Robins, *J. Am. Chem. Soc.*, 83, 4038, (1961), (1.67 g, 22 mmol) in 2N KOH (11 mL) was added and continued stirring for 25 min at 0.C. The mixture was allowed to stand at 0° C. without stirring for 1.5 h. The precipitate was collected by filtration and washed with small amount of water and EtOH to obtain 1.45 g (36%) of the title compound, mp>250° C.: UV: $\lambda_{max}$ (pH 1) 325 nm (ε 6,400), 240 nm (sh): $\lambda_{max}$ (pH 7) 310 nm (ε 5,900), 237 nm (ε 6,800): $\lambda_{max}$ (pH 11) 312 nm (ε 5,900): $^1$H NMR (DMSO-d$_6$): δ 5.78 (br s, 2, NH$_2$, exchangeable in D$_2$O), 7.73 (s, 1, C$_8$H): Anal. Calcd for C$_5$H$_6$N$_6$S.½ H$_2$O (191.1): C, 31.41: H, 3.27: N, 43.98: S, 16.79. Found: C, 1.89: H, 3.27: N, 43.38: S, 17.19.

EXAMPLE 2

2-Aminopurine-6-sulfinamide (3)

2-Aminopurine-6-sulfenamide 2 (182 mg, 1 mmol) was suspended in EtOH (100 mL) and cooled to 0° C. m-Chloroperoxybenzoic acid (85%, 200 mg, 1 mmol) was added portionwise during 1 h with stirring, and stirring continued for additional 30 min. After filtration, the filtrate was concentrated to half the volume in vacuo. Ethyl ether (50 mL) was added and allowed to stand in a refrigerator overnight. The precipitate was collected by filtration and washed with ether to obtain 115 mg (58%) of the desired compound, mp. >250° C., : UV $\lambda_{max}$ (pH 1) 332 nm (ε 4,600) 240 nm (sh): $\lambda_{max}$ (pH 7) 326 nm (ε 4,500): $\lambda_{max}$ (pH 11) 326 nm (ε 4,200), 283 nm (ε 2,800): IR(KBr): 1140 (SO) cm$^{-1}$: $^1$H NMR (DMSO-d$_6$): δ 6.59 (br s, 2,—SONH$_2$, exchangeable in D$_2$O), 6.57 (br s, 2, NH$_2$, exchangeable in D$_2$O), 8.12 (s, 1, C$_8$H), 12.50 (br s, 1, NH, exchangeable in D$_2$O). Anal. Calcd for C$_5$H$_6$N$_6$OS (198.21): C, 30.30: H, 3.05: N, 42.40: S, 16.18. Found: C, 30.02: H, 2.82: N, 42.64: S, 15.97.

EXAMPLE 3

2-Aminopurine-6-sulfonamide (4)

To a suspension of 2-aminopurine-6-sulfenamide 2 (500 mg, 2.7 mmol) in EtOH (250 mL) was added m-chloroperoxybenzoic acid (85%, 2.25 g, 11 mmol) and stirred for 1.5 h at room temperature. After filtration, the filtrate was evaporated to dryness. The residue was triturated with ether and then purified on a silica gel column using ethyl acetate : (EtOAc:H$_2$O:1-PrOH, 4:2:1, upper phase) (90:10, v/v) as eluent. The precipitation from EtOH-ether gave 162 mg (28%) of the title compound, mp >250° C.: UV $\lambda_{max}$ (pH 1) 338 nm (ε 4,200): $\lambda_{max}$ (pH 7) 329 nm (ε 4,000): $\lambda_{max}$ (pH 11) 325 nm (ε 4,100), 285 (2,800): IR (KBr) 1150 (S=O), 1320 (SO$_2$) cm$^{-1}$: $^1$H NMR (DMSO-d$_6$): δ 6.67 (br s, 2, NH$_2$, exchangeable in D$_2$O), 7.61 (br s, SO$_2$NH$_2$, exchangeable in D$_2$O), 8.29 (s, 1, C$_8$H), 12.75 (br s, 1, NH, exchangeable in D$_2$O): Anal Calcd for C$_5$H$_6$N$_6$O$_2$S (214.21): C, 28.03: H, 2.2: N, 39.24: S, 14.97. Found: C, 28.20: H, 2.72: N, 38.98: S, 15.03.

EXAMPLE 4

9-β-D-Ribofuranosyl-9H-purine-6-sulfenamide (6)

Commercial 0.77M sodium hypochlorite (5.25%, 15 mL) was cooled to <0° C. and added with stirring to similarly cooled 0.77M ammonium hydroxide (29%, 3.7 mL diluted to 40 mL with H$_2$O). The resulting solution of chloramine was mixed with a solution of 9-β-D-ribofuranosyl-9H-purine-6-thione 5(2.84 g, 10 mmol) in 2M potassium hydroxide (5 mL) at <0° C. The mixture was stirred for 40 min until it had warmed to room temperature and the solvents were evaporated. The residue was dissolved in MeOH (50 mL) and adsorbed onto silica gel (2 g). The excess solvent was evaporated under reduced pressure and the residue was loaded onto a silica gel column (3×40 cm) packed in CH$_2$Cl$_2$. The column was eluted with CH$_2$Cl$_2$:MeOH (8:2, 7:3, v/v). The appropriate homogeneous fractions were combined and the solvents evaporated to give 6 as a foam (1.5 g, 50% yield): m.p. 100° C.: UV: $\lambda_{max}$ (pH 1) 301 nm (ε 11,100): $\lambda_{max}$ (pH 7) 288 nm (ε 8,700): $\lambda_{max}$ (pH 11) 288 nm (ε 9,500): $^1$H NMR (DMSO-d$_6$): δ 4.15 (s, 2, S-NH$_2$, exchanged with D$_2$O), 6.00 (d, 1, J=5.73 Hz, C$_1$'H), 8.70 (s, 1, C$_2$H), 8.77 (s, 1, C$_8$H), and other sugar protons. Anal. Calcd for C$_{10}$H$_{13}$N$_5$O$_4$S (299.3): C, 40.13: H, 4.38: N, 23.40: S, 10.71. Found: C, 40.29: H, 4.46: N, 23.10: S, 10.45.

EXAMPLE 5

9-β-D-Ribofuranosyl-9H-purine-6-sulfinamide (7)

To an ice-cooled stirred solution of (0.299 g, mmol) in ethanol (30 mL), a solution of m-chloroperoxybenzoic acid (0.2 g, 1 mmol) in ethanol (10 mL) was added dropwise during 10 min. After 40 min the solvent was evaporated, the residue was dissolved in MeOH (30 mL) and adsorbed onto silica gel (10 g). The excess solvent was evaporated under reduced pressure and the dry residue was loaded onto a flash silica gel column (2×40 cm) packed in CH$_2$Cl$_2$. The column was eluted with CH$_2$Cl$_2$:MeOH (8.2 and then 7:3, v/v). The appropriate homogeneous fractions were combined and the solvents were evaporated to give 7 as a foam, m.p. 80.C, (0.21 g, 67% yield). IR (KBr): 1050 (vs, S=O), 1330 (s, S⊙0), 3000-3600 (OH, NH$_2$)cm$^{-1}$: UV: $\lambda_{max}$ (pH 1) 272 nm (ε 3,600): $\lambda_{max}$ (pH 7) 273 nm (ε 4,100): $\lambda_{max}$ (pH 11) 273 nm (ε 3,200): $^1$H NMR (DMSO-d$_6$): δ 6.08 (d, 1, J=5.4 Hz, C$_1$'H), 6.68 (s, 2, SONH$_2$, exchanged with D$_2$O), 9.00 (s, 1, C$_2$H), 9.08 (s, 1, C$_8$H), and other sugar protons. Anal. Calcd for C$_{10}$H$_{13}$N$_5$O$_5$S.½ H$_2$O (324.3): C, 37.04: H, 4.32: N, 21.60: S, 9.88. Found: C, 37.43: H, 4.53: N, 21.36: S, 9.97.

EXAMPLE 6

9-β-D-Ribofuranosyl-9H-purine-6-sulfonamide (8)

To a solution of 6 (0.299 g, 1 mmol) in ethanol (35 mL) at room temperature, a solution of m-chloroperoxybenzoic acid (0.8 g, 4 eq.) in ethanol (20 mL) was added, with stirring. After 30 min the reaction mixture was evaporated and the residue was purified by flash column chromatography and treated in the same way as described for 7, to give 8 as a foam, (0.11 g, 33% yield): IR (KBr): 1060, 1080 (s, S=O), 1340 (vs, b, $SO_2$), 3000–3600 (OH, $NH_2$)cm$^{-1}$: UV: $\lambda_{max}$ (pH 1) 275 nm ($\epsilon$ 14,000): $\lambda_{max}$ (pH 7) 275 nm ($\epsilon$ 12,900): $\lambda_{max}$ (pH 11) 272 nm ($\epsilon$ 17,800): $^1$H NMR (DMSO-d$_6$): δ 6.10 (d, 1, J = 5.4 Hz, $C_1$H), 7.80 (br s, 2, $SO_2NH_2$, exchanged with $D_2O$), 9.04 (s, 1, $C_2$H), 9.10 (s, 1, $C_8$H) and other sugar protons. Anal. Calcd for $C_{10}H_{13}N_5O_6S \cdot C_2H_5OH \cdot \frac{1}{2} H_2O$ (386.3): C, 37.28: H, 5.18: N, 18.12: S, 8.28. Found: C, 37.24: H, 4.51: N, 18.26: S, 8.13.

EXAMPLE 7

9-β-D-Arabinofuranosyl-9H-purine-6-sulfenamide (10)

Commercial 0.77M sodium hypochlorite (5.25%, 46 mL) was cooled to <0° C. and added with stirring to similarly cooled 0.77M ammonium hydroxide (29%, 11.1 mL diluted to 120 mL with $H_2O$). The resulting solution of chloramine was mixed with a solution of 9-β-D-arabinofuranosyl-9H-purine-6-thione 9 (8.52 g, 30 mmol) in 2M potassium hydroxide (15 mL) at <0° C. The mixture was stirred until it had warmed to room temperature (40 min). After 1 h the product that crystallized out was filtered, washed with ethanol, dried at room temperature and recrystallized from ethanol to give (5 g, 56% yield) of 10. m.p. 176°–178° C. (dec.): UV: $\lambda_{max}$ (pH 1) 295 nm ($\epsilon$ 6,000): $\lambda_{max}$ (pH 7) 285 nm ($\epsilon$ 5,800): $\lambda_{max}$ (pH 11) 285 nm 5,500): $^1$H NMR (DMSO-d$_6$): δ4.15 (s, 2, S-$NH_2$, exchanged with $D_2O$), 6.37 (d, 1, J = 5.19 Hz, $C_1$H), 8.50 (s, 1, $C_2$H), 8.71 (s, 1, $C_8$H), and other sugar protons. Anal. Calcd for $C_{10}H_{13}N_5O_4S$ (299.3): C, 40.13: H, 4.38: N, 23.40: S, 10.71. Found: C, 39.94: H, 4.38: N, 22.90: S, 11.00.

EXAMPLE 8

9-β-D-Arabinofuranosyl-9H-purine-6-sulfinamide (11)

To an ice cooled stirred solution of 10 (1.5 g, 5 mmol) in ethanol:$H_2O$ (525 mL, 20:1, v/v), m-chloroperoxybenzoic acid (1 g, 1 eq.) in ethanol (50 mL) was added dropwise during 20 min. After 4 h the separated crystals were filtered off, the filtrate was evaporated to dryness, triturated with methanol, filtered, washed with methanol and dried at room temperature to yield 11, (0.5 g, 31% yield), m.p. >120° C. The filtrate was evaporated and purified by chromatography as described for 6 to yield another crop of 11, (0.25 g, 15%: overall yield 46%). IR (KBr): 1060 (vs, br, S=O), 1330 (s, S=O), 3000–3600 ($NH_2$, OH) cm$^{-1}$: UV: $\lambda_{max}$ (pH 1) 272 nm ($\epsilon$ 3,000): $\lambda_{max}$ (pH 7) 275 nm ($\epsilon$7,100): $\lambda_{max}$ (pH 11) 272 nm ($\epsilon$ 1,700): $^1$H NMR (DMSO-d$_6$): δ 6.46 (d, 1, J = 5.16 Hz, $C_1$H), 6.71 (s, 2, $SONH_2$, exchanged with $D_2O$), 8.83 (s, 1, $C_2$H), 9.06 (s, 1, C8H), and other sugar protons. Anal. Calcd for $C_{10}H_{13}N_5O_5S \cdot 0.3H_2O$ (321.32): C, 37.38: H, 4.24: N, 21,80: S, 9.97. Found: C, 37.03: H, 4.19: N, 21.42: S, 10.37.

EXAMPLE 9

9-β-D-Arabinofuranosyl-9H-purine-6-sulfonamide (12)

To a solution of 10 (3.6 g, 12 mmol) in ethanol (1200 mL) and water (80 mL) at room temperature was added m-chloroperoxybenzoic acid (8.8 g, 4 eg.) with stirring. The reaction mixture was left overnight at room temperature. The precipitated product (12) was filtered, washed well with ethanol to yield 3 g (75%) of 12. The filtrate was concentrated to get another crop of (12), 0.3 g (6%) overall yield (81%): m.p. 160° C. (dec.): IR (KBr): 1050 (s, S=O), 1340 (vs, br, $SO_2$), 3000–3600 (OH, $NH_2$)cmp$^{-1}$: UV; $\lambda_{max}$ (pH 1) 275 nm ($\epsilon$ 5,600): $\lambda_{max}$ (pH 7) 276 nm ($\epsilon$ 6,500): $\lambda_{max}$ (pH 11) 274 nm ($\epsilon$ 6,900): $^1$H NMR (DMSO-d$_6$): δ 6.70 (d, 1, J = 5.28 Hz, $C_1$H), 7.85 (s, 2, $SO_2NH_2$, exchanged with $D_2O$), 8.88 (s, 1, $C_2$H), 9.08 (s, 1, $C_8$H), and other sugar protons. Anal. Calcd for $C_{10}H_{13}N_5O_6S \cdot \frac{1}{2}H_2O$ (340.3): C, 35.29: H, 4.12: N, 20.59: S, 9.41. Found: C, 35.63: H, 4.07: N, 20.27: S, 8.97.

EXAMPLE 10

9-(2-Deoxy-β-D-erythro-pentofuranosyl)-9H-purine-6-sulfenamide (14)

Commercial 0.77M sodium hypochlorite (5.25%, 15 mL) was cooled to <0° C. and added with stirring to similarly cooled 0.77M ammonium hydroxide (29%, 3.7 mL diluted to 40 mL with $H_2O$). The resulting solution of chloramine was mixed with a solution of 9-(2-deoxy-β-D-erythro-pentofuranosyl)-9H-purine-6-thione 13 (2.68 g, 10 mmol) in 2M potassium hydroxide (5 mL) at <0° C. The mixture was stirred until it had warmed to room temperature (50 min). The solvents were evaporated and the residue was purified by flash chromatography as described for 6 to give 14 as a foam (2.1 g, 71% yield). UV: $\lambda_{max}$ (pH 1) 300 nm (e8,000): $\lambda_{max}$ (pH 7) 288 nm ($\epsilon$8,200): $\lambda_{max}$ (pH 11) 288 nm ($\epsilon$10,300): $^1$H NMR (DMSO-d$_6$): δ 3.87 (s, 2, $SNH_2$, exchanged with $D_2O$), 6.43 (t 1 J=3 54 Hz $C_1$H) 8.75 (s, $C_2$H), 8.84 (s, 1, $C_8$H), and other sugar protons. Anal. Calcd for $C_{10}H_{13}N_5O_3S$ (283.3): C, 42.39: H, 4.62: N, 24.72: S, 11.32. Found: C, 42.12: H, 4.85: N, 24.48: S, 11.51.

EXAMPLE 11

9-(2-Deoxy-β-D-erythro-pentofuranosyl)-9H-ourine-6-sulfinamide (15)

To an ice-cooled stirred solution of 14 (0.368 g, 1.3 mmol) in ethanol (20 mL), m-chloroperoxybenzoic acid (0.26 g, 1 eq.) in ethanol (10 mL) was added dropwise during 10 min. The mixture was warmed to room temperature (90 min). The product which crystallized out was filtered, washed with ethanol, dried at room temperature to yield 15 (0.18 g, 46% yield), m.p. 120° C.: IR (KBr): 1060 (vs, S=O), 1360 (S=O), 3000–3500 ($NH_2$, OH)cm$^{-1}$: UV: $\lambda_{max}$ (pH 1) 272 nm ($\epsilon$7,400): $\lambda_{max}$ (pH 7) 273 nm ($\epsilon$8,600): $\lambda_{max}$ (pH 11) 274 nm ($\epsilon$9,100): $^1$H NMR (DMSO-d$_6$): δ 6.50 (t, 1, J=6.60 Hz, $C_1$H), 6.68 (s, 2, $SONH_2$, exchanged with $D_2O$), 8.94 (s, 1, $C_2$H), 9.06 (s, 1, $C_8$e,uns/H/ ), and other sugar protons. Anal. Calcd for $C_{10}H_{13}N_5O_4S$ (299.3): C, 40.13: H, 4.38: N, 23.40: S, 10.71. Found: C, 40.39: H, 4.40: N, 23.32: S, 10.51.

EXAMPLE 12

9-(2-Deoxy-β-D-erythro-pentofuranosYl)-9H-purine-6-sulfonamide (16)

To a stirred solution of 14 (1.3 g, 4.6 mmol) in ethanol (120 mL) was added a solution of m-chloroperoxybenzoic acid (3 g, 4 eq.) in ethanol (50 mL) at room temperature. After 1 h the reaction mixture was evaporated and the residue was purified by flash column chromatography as described for 8 to yield 16, (0.6 g, 41%) as a foam. IR (KBr): 1140 (s, S=O), 1320 (vs, SO$_2$), 2800–3500 (NH$_2$, OH)cm$^{-1}$: UV: $\lambda_{max}$ (pH 1) 275 nm (ε5,800): $\lambda_{max}$ (pH 7) 275 nm (ε7,600): $\lambda_{max}$ (pH 11) 273 nm (ε7,900): $^1$H NMR (DMSO-d$_6$): δ 6.53 (t, 1, J=6.45 Hz, C$_1$·H), 7.85 (s, 2, SO$_2$NH$_2$, exchanged with D$_2$O), 9.00 (s, 1, C$_2$H), 9.08 (s, 1, C$_8$H), and other sugar protons. Anal. Calcd for C$_{10}$H$_{13}$N$_5$O$_5$S.½H$_2$O (324.3): C, 37.03: H, 4.32: N, 21.60: S, 9.88. Found: C, 36.67: H, 4.11: N, 22.01: S, 10.26.

EXAMPLE 13

2-Amino-9-β-D-ribofuranosyl-9H-ourine-6-sulfenamide (18)

Sodium hypochlorite, 0.77M (76 mL, 0.532 mmol, freshly opened bottle of commercial bleach) was placed in a stoppered 1 L flask and the flask was submerged in an ice bath. Ammonium hydroxide, 0.77M (200 mL, 1.4 mmol) was similarly cooled in an ice bath. Acetone was added to the ice baths to obtain a temperature of <0° C. in both solutions. The ammonia solution was then added rapidly to the bleach solution and the flask was immediately stoppered. The mixture was stirred in the cold (0° to −5° C.) for approx. 15 min and then a suspension of thioguanosine 17 (15 g, 0.0501 mmol) in 2 KOH was added quickly and rinsed into the chloramine mixture with a small amount of water. The flask was immediately stoppered. The reaction mixture was initially a clear yellow solution but after a few minutes a white solid began separating. The reaction mixture was stirred in the cold (0° to −5° C.) for 30 min and then the solid was collected and washed with ethanol (50 mL). The solid was further washed by suspension in ethanol (3×50 mL) and air dried to yield 11.7 g, (0.0372 mmol, 74%) of 18, m.p. 196°–198° C. dec.: UV: $\lambda_{max}$ (pH 1) 332 nm (ε3,000): $\lambda_{max}$ (pH 7) 311 nm (ε3,500): $\lambda_{max}$ (pH 11) 311 nm (ε3,500): $^1$H NMR (DMSO-d$_6$): δ 3.91 (s, 2, SNH$_2$, exchanged with D$_2$O), 5.80 (d, 1, J=5.97 Hz, C$_1$·H), 6.50 (s, 2, NH$_2$, exchanged with D$_2$O), 8.18 (s, 1, C$_8$H), and other sugar protons. Anal. Calcd. for C$_{10}$H$_{14}$N$_6$O$_4$S (314.32): C, 38.21: H, 4.49: N, 26.74: S, 10.20. Found: C, 38.16: H, 4.68: N, 26.49: S, 10.49.

EXAMPLE 14

2-Amino-9-β-D-ribofuranosyl-9H-purine-6-sulfinamide (19)

A mixture of 2-amino-9-β-D-ribofuranosyl-9H-purine-6-sulfenamide (18) (1.57 g, 0.005 mol), ethanol (700 mL) and water (50 mL) was vigorously stirred and cooled in an ice bath. After the temperature of the suspension had decreased to <10° C., acetone was added to the ice bath to obtain a temperature of <0° C. With continual stirring a solution of commercially available (Aldrich Chem Co.) 3-chloroperoxybenzoic acid (80–85%, 1.0 g, 0.0046–0.0049 mol) in ethanol (40 mL) was added dropwise over a period of approx. 15 min. The reaction flask was stoppered, the mixture was allowed to stir and warm as the ice melted, and then stirred at ambient temperature for a total reaction time of 19 hr. The reaction mixture was filtered (Whatman GF/A glass microfiber filter) to remove a trace of undissolved solid and then the filtrate was evaporated in vacuo and at a temperature of >25° C. to near dryness. The product was washed from the evaporation flask with acetone (50–100 mL) and the solid was collected by filtration, suspended in diethyl ether (50 mL), refiltered, dried under vacuum at ambient temperature: (1.3 g, 0.0042 mol, 85%), m.p. 183°–185° C. dec. with prior sintering and darkening. IR (KBr): 1040 (vs, S=O), 3000–3600 (NH$_2$, OH)cm$^{-1}$: UV: $\lambda_{max}$(pH 1) 333 nm (ε2,900): $\lambda_{max}$ (pH 7) 326 nm (ε10,700): $\lambda_{max}$ (pH 11) 325 nm (ε8,700): $^1$H NMR (DMSO-d$_6$): δ 5.85 (d, 1, J =5.52 Hz, C$_1$·H), 6.49 (s, 2, SONH$_2$, exchanged with D$_2$O), 6.98 (s, 2, NH$_2$, exchanged with D$_2$O), 8.45 (s, 1, C$_8$e,uns/H/ ), and other sugar protons. Anal. Calcd. for C$_{10}$H$_{14}$N$_6$O$_5$S.¼C$_2$H$_5$OH (353.32): C, 37.39: H, 4.82: N, 23.80: S, 9.07. Found: C, 37.29: H, 4.56: N, 23.78: S, 8.92.

EXAMPLE 15

2-Amino-9-β-D-ribofuranosyl-9H-ourine-6-sulfonamide (20)

To a stirred suspension of 18 (3.14 g, 10 mmol) in EtOH:CH$_2$Cl$_2$ (800 mL, 3:1, v/v) at room temperature was added a solution of m-chloroperoxybenzoic acid (8 g, 4 eq.) in ethanol (60 mL). After 4 h, the separated crystals were filtered, washed with ethanol to get 2.55 g (74%) of a mixture of 19 and 20. By fractional crystallization from methanol, 20 (2 g, 64%) was obtained. Recrystallization of 20 from H$_2$O-MeOH (100 mL, 8:2, v/v) gave colorless crystals (1 g, 34%), m.p. 210° C. (dec.): IR (KBr): 1320 (vs, SO$_2$), 3000–3600 (NH$_2$, OH)cm$^{-1}$: UV: $\lambda_{max}$ (pH 1) 332 nm (ε7,700): $\lambda_{max}$ (pH 7) 328 nm (ε8,600): $\lambda_{max}$ (pH 11) 320 nm (ε12,700): $^1$H NMR (DMSO-d$_6$): δ 5.85 (d, 1, J =5.85 Hz, C$_1$·H), 6.99 (s, 2, SO$_2$NH$_2$, exchanged with D$_2$O), 7.52 (s, 2, NH$_2$, exchanged with D$_2$O), 8.48 (s, 1, C$_8$e,uns/H/ ), and other sugar protons. Anal. Calcd. for C$_{10}$H$_{14}$N$_6$O$_6$S (346.32): C, 34.68: H, 4.07: N, 24.27: S, 9.26. Found: C, 34.49: H, 4.18: N, 24.09: S, 9.51.

EXAMPLE 16

2-Amino-9-(2-deoxy-β-D-erythro-pentofuranosyl)-9H-purine-6-sulfenamide (22)

Commercial 0.77M sodium hypochlorite (5.25%, 15 mL) was cooled to <0° C. and added with stirring to similarly cooled 0.77M ammonium hydroxide (29%, 3.7 mL diluted to 40 mL with H$_2$O). The resulting solution of chloramine was mixed with a solution of 2-amino-9-(2-deoxy-β-D-erythro-pentofuranosyl)-9-H-purine-6-thione 21, prepared as per K. Ramasamy et al., J. Heterocycl. Chem, (in press), (2.83 g, 10 mmol) in 2M potassium hydroxide (5 mL) at 0.C. After 90 min the solvents were evaporated and the residue was dissolved in MeOH (50 mL) and adsorbed onto silica gel (1 g). The excess solvent was evaporated under reduced pressure and the residue was loaded onto a silica gel column (4×15 cm) packed in CH$_2$Cl$_2$. The column was eluted with CH$_2$Cl$_2$:MeOH (8:2, 7:3, v/v). The appropriate homogeneous fractions were combined and the solvents evaporated to yield 22 (2.6 g, 86%), m.p. 130° C. (dec.): UV: $\lambda_{max}$ (pH 1) 328 nm (ε11,700): $\lambda_{max}$ (pH 7) 309 nm (ε10,600): $\lambda_{max}$ (pH 11) 309 nm (ε10,900): $^1$H NMR (DMSO-d$_6$): δ 3.90 (s, 2, SNH$_2$, exchanged with D$_2$O), 6.23 (t, 1, J =6.60 Hz, C$_1$·H), 6.50 (s, 2, NH$_2$, exchanged with D$_2$O), 8.16 (s, 1, C$_8$H, and other sugar protons. Anal. Calcd. for C$_{10}$H$_{14}$N$_6$O$_3$S (298.32): C, 40.27: H, 4.70: N, 28.19: S, 10.74. Found: C, 40.10: H, 4.40: N, 27.89: S, 10.53.

EXAMPLE 17

2-Amino-9-(2-deoxy-ε-D-erythro-pentofuranosyl)-9H-purine-6-sulfinamide (23)

To an ice-cooled stirred suspension of 22 (0.298 g, 1 mmol) in ethanol (200 mL) and CH$_2$Cl$_2$ (50 mL), m-chloroperoxybenzoic acid (0.5 g, 1 eq.) in ethanol (30 mL) was added dropwise during 15 min. After 80 min the clear solution of the reaction mixture was adsorbed onto silica gel (1 g) and the excess solvent was evaporated under reduced pressure and the residue loaded onto a silica gel column (2.5×15 cm) packed in CH$_2$Cl$_2$. The column was eluted with CH$_2$Cl$_2$:MeOH (8:2, 75:25, v/v). The appropriate homogeneous fractions were combined and the solvent evaporated to yield 23 (0.65 g, 69%), m.p. 80° C. (dec.): IR (KBr) 1050 (vs, S=O), 3000–3600 (NH$_2$, OH)cm$^{-1}$: UV: $\lambda_{max}$ (pH 1) 339 nm (ε4,300): $\lambda_{max}$ (pH 7) 327 nm (ε6,000): $\lambda_{max}$ (pH 11) 326 nm (ε6,000): $^1$H NMR (DMSO-d$_6$): δ 6.27 (t, 1, J =6.75 Hz, C$_1$·H), 6.51 (s, 2, SONH$_2$, exchanged with D$_2$O), 6.98 (s, 2, NH$_2$, exchanged with D$_2$O), 8.43 (s, 1, C$_8$H), and other sugar protons. Anal. Calcd. for C$_{10}$H$_{14}$N$_6$O$_4$S (314.32): C, 38.21: H, 4.49: N, 26.74: S, 10.20. Found: C, 38.48: H, 4.83: N, 26.75: S, 10.21.

EXAMPLE 18

2-Amino-9-(2-deoxy-β-D-erythro-pentofuranosyl)-9H-purine-6-sulfonamide (24)

To a stirred suspension of 22 (0.895 g, 3 mmol) in ethanol (250 mL) at room temperature was added m-chloroperoxybenzoic acid (2.4 g, 4 eq.). After 6 h the clear solution of the reaction mixture was evaporated to dryness. The residue dissolved in EtOH (10 mL) and adsorbed onto silica gel (1 g.). The excess solvent was evaporated under reduced pressure and loaded onto a silica gel column (2.5×15 cm) packed in CH$_2$Cl$_2$. The column was eluted with CH$_2$Cl$_2$:MeOH (85:15, 8:2, v/v). The appropriate homogeneous fractions were combined and the solvent evaporated to yield 24 (0.25 g, 25%) as semisolid: IR (KBr): 1350 (s, SO$_2$), 3000–3600 (NH$_2$, OH)cm$^{-1}$:UV: $\lambda_{max}$ (pH 1) 332 nm (ε4,300): $\lambda_{max}$ (pH 7) 329 nm (ε5,200): $\lambda_{max}$ (pH 11) 320 nm (ε6,500): $^1$H NMR (DMSO-d$_6$): δ 6.28 (t, 1, J =6.75 Hz, C$_1$·H), 6.99 (s, 2, SO$_2$NH$_2$, exchanged with D$_2$O), 7.52 (s, 2, NH$_2$, exchanged with D$_2$O), 8.46 (s, 1, C$_8$H), and other sugar protons. Anal. Calcd. for C$_{10}$H$_{14}$N$_6$O$_5$S.H$_2$O.½C$_2$H$_5$OH (330.32): C, 35.58: H, 5.12: N, 22.64: S, 8.63. Found: C, 35.49: H, 5.33: N, 22.57: S, 8.43.

EXAMPLE 19

2-Amino-9-β-D-ribofuranosylpurine-6-sulfinamide 5'-Monophosphate Potassium Salt (27)

To an ice-cold 5.25% sodium hypochlorite solution (2.3 mL) was added 4N NH$_4$OH (2 mL) and stirred for 10 min. 2-Amino-9-β-D-ribofuranosylpurine-6-thione 5'-Monophosphate 25, prepared as per M. Saneyoshi, *Chem. Pharm. Bull.*, 19, 493 (1971), (569 mg, 1.5 mmol) in 2N KOH (0.75 mL) was added and stirring continued for 2 h at 0° C. The mixture was evaporated to dryness and the residue was applied on XAD-4 column and eluted with water. The fractions containing desired compound were combined and evaporated to dryness to obtain 420 mg of the sulfenamide dipotassium salt 26. The white powder 26 (378 mg) was dissolved in 20 mL of water and cooled to 0° C. m-Chloroperoxybenzoic acid (85%, 250 mg, 1.2 mmol) in MeOH (10 mL) was added and stirred for 40 min. After the filtration, the filtrate was concentrated to 3 mL in vacuo and purified on XAD-4 column using water as eluent to provide 145 mg of the title hygroscopic compound 27: m.p. >250° C.: UV: $\lambda_{max}$ (pH 1) 332 nm: $\lambda_{max}$ (pH 7) 321 nm: $\lambda_{max}$ (pH 11) 320 nm: IR (KBr) 1045 (S=O) cm$^{-1}$: $^1$H NMR (DMSO-d$_6$): δ5.88 (d, 1, C$_1$·H, J =6.0Hz), 6.73 (br s, 2, NH$_2$, exchangeable in D$_2$O), 8.50 (s, 1, C$_{8e,uns}$/H/ ) FAB-MS (on glycerol) m/z 449 [M+H]$^+$: 411 [M−K+H]$^+$: (NaCl addition) m/z 494 [M+2Na]$^+$, 472 [M+Na+H]$^+$.

EXAMPLE 20

2-Amino-9-β-D-ribofuranosylpurine-6-sulfenamide 3',5'-cyclic phosphate (29)

Commercial 0.77M sodium hypochlorite (5.25%, 1.2 mL) was cooled to <0° C. and added with stirring to similarly cooled 0.77M ammonium hydroxide (29%, 0.3 mL diluted to 3 mL with H$_2$O). The resulting solution of chloramine was mixed with a solution of 2-amino-9-β-D-ribofuranosylpurine-6-9-H-thione 3',5'-cyclic phosphate 28, prepared as per R. B. Meyer et al, *J. Cyclic Nucleotide Res.*, 1, 159 (1975), (0.3 g, 0.83 mmol) in 2M potassium hydroxide (0.37 mL) at <0° C. The mixture was stirred for h and the solvents were evaporated. The residue was dissolved in MeOH and adsorbed onto silica gel (1 g). The excess solvent was evaporated under reduced pressure and the solids were loaded onto a silica gel column (1.5×15 cm) packed in CH$_2$Cl$_2$. The column was eluted with CH$_2$Cl$_2$:MeOH (8:2, 4:6, v/v). The appropriate homogeneous fractions were combined and the solvents evaporated to give the title compound 29 (0.25 g, 80%): m.p. 265° C. (dec): UV: $\lambda_{max}$ (pH 1) 329 nm (ε10,400): $\lambda_{max}$ (pH 7) 309 nm (ε9,000): $\lambda_{max}$ (pH 11) 309 nm (ε8,800): $^1$H NMR (DMSO-d$_6$): δ3.93 (s, 2, S-NH$_2$, exchanged with D$_2$OL), 5.82 (s, 1, C$_1$·H), 6.58 (s, 2, NH$_2$, exchanged with D$_2$O), 8.08 (s, 1, C$_{8e,uns}$/H/ ), and other sugar protons.

EXAMPLE 21

2-Amino-9-β-D-ribofuranosylpurine-6-sulfinamide 3',5'-cyclic phosphate (30)

To an ice- stirred suspension of 29 (0.13 g, 0.35 mmol) in ethanol (20 mL), m-chloroperoxybenzoic acid (0.07 g, 1 eq.) in ethanol (5 mL) was added dropwise during 10 min. The reaction mixture was stirred for 5 h. The precipitated product was filtered, washed with ethanol, dried to yield the title compound 30, (0.1 g, 72%): IR (KBr): 1030 (s, S=O), 1360 (s, SO$_2$), 3000–3600 (OH, NH$_2$)cm$^{-1}$: UV: $\lambda_{max}$ (pH 1) 330 nm (ε9,000): $\lambda_{max}$ (pH 7) 325 nm (ε4,500): $\lambda_{max}$ (pH 11) 324 nm (ε4,700): $^1$H NMR (DMSO-d$_6$): 5.88 (s, 1, C$_1$·H), 6.60 (s, 2, SONH$_2$, exchanged with D$_2$O), 7.13 (s, 2, NH$_2$, exchanged with D$_2$O), 8.36 (s, 1, C$_{8e,uns}$/H/ ), and other sugar protons.

EXAMPLE 22

6-Amino-1-(2,3,5-tri-0-acetyl-β-D-ribofuranosyl)-pyrazolo[3,4-d]pyrimidine-4-one A solution of acetic anhydride (60 mL) and 4-dimethylaminopyridine (300 mg) in dry dimethylformamide (300 mL) was cooled below 10° C. 6-Amino-1-β-D- ribofuranosylpyrazolo[3,4-d]pyrimidine-4-one, prepared as per H. B. Cottam et al, *Nucleic Acid Research*, 11, 871–882 (1983), (6.0 g, 21 mmol) was added and stirred for 3 h below 10° C. Methanol (150 mL) was added and stood for 30 min at 0° C. After the removal of solvent in vacuo, the residue was dissolved in EtOAc (500 mL) and filtrated. The filtrate was washed with water, dried over anhydrous $Na_2SO_4$, and evaporated to dryness. The mixture was purified on silica gel column with $CH_2Cl_2$:MeOH (97:3, v/v) as the solvent to yield 3.2 g (37%) of title compound. The analytical sample was obtained by crystallization from acetone-hexane : mp 191<193° C.: UV: $\lambda_{max}$ (MeOH) 253 nm ($\epsilon$16,700): $^1$H NMR (DMSO-d$_6$) δ2.00, 2.07 and 2.09 (3s, 9H, 3-CH$_3$ of Ac), 6.10 (d, IH, J=3.6 Hz, C$_1$·H̲), 6.81 (br s, 2, —NH$_2$, exchangeable in D$_2$O) 7.94(s, 1, C$_3$H̲), 10.73(s, 1, NH̲) : Anal. Calcd for C$_{16}$H$_{19}$N$_5$O$_8$ (409.35): C, 46.94: H, 4.68: N, 17.11. Found C, 47.03: H, 4.67: N, 16.90.

6-Amino-1-(2,3,5-tri-0-acetyl-β-D-ribofuranosyl)-pyrazolo-3,4-d1pyrimidine-4-thione 6-Amino-1-(2,3,5-tri-0-acetyl-β-D-ribofuranosyl)-pyrazolo-[3,4-d]pyrimidine-4-one (5.0 g, 12.2 mmol) and phosphorus pentasulfide (3.5 g, 15.7 mmol) in anhydrous pyridine was refluxed for 5 h. After removal of half volume of solvent in vacuo, the mixture was poured into 600 mL of water and then extracted with $CH_2Cl_2$ (200 mL, 6 times). The combined extract were washed with water, dried over anhydrous $Na_2SO_4$, evaporated to dryness. The residue was purified on silica gel column with $CH_2Cl_2$:MeOH (98:2, v/v) as solvent to yield 3.0 g (58%) of desired compound. mp 230<232° C.: UV $\lambda_{max}$ (MeOH) 336 nm ($\epsilon$21,700), 272 nm ($\epsilon$10,700): $^1$H NMR (DMSO-d$_6$) δ2.00, 207, and 2.09 (3s, 9H, 3-CH$_3$ of Ac), 6.08 (d, 1, J=3.6 Hz, C$_1$·H̲), 7.09 (br s, 2, NH$_2$), 8.07 (s, 1, C$_3$H̲), 12.16 (br s, 1, NH̲): Anal. Calcd for C$_{16}$H$_{19}$O$_7$N$_5$S (425.41): C, 45.17: H, 4.50: N, 16.46: S, 7.54. Found: C, 45.23: H, 4.50: N, 16.30: S, 7.46.

6-Amino-1-β-D-ribofuranosylpyrazolo[3.4-d1pyrimidine-4-thione (31)

6-Amino-1-(2,3,5-tri-0-acetyl-β-D-ribofuranosyl)-pyrazolo[3,4-d]pyrimidine-4-thione (2.4g, 5.6 mmol) was suspended in MeOH (150 mL) and IN NaOMe was added to pH 10. The mixture was refluxed for 8 h and maintained at pH 10 by addition of 1N NaOMe. After cooled to room temperature, the mixture was neutralized with Dowex 50[H+] resin and the solvent was evaporated. The residue was purified on silica gel column with $CH_2Cl_2$:MeOH (9:1, v/v) to yield 1.2 g (71%) of the title compound. mp 222°–224° C.: UV $\lambda_{max}$ (pH 1) 328 nm (5,900), 268 nm ($\epsilon$2,300), 237 nm ($\epsilon$6,300): $\lambda_{max}$ (pH 7)328 nm ($\epsilon$5,900), 268 nm ($\epsilon$2,600), 237 nm ($\epsilon$6,700): $\lambda_{max}$ (pH 11) 319 nm ($\epsilon$4,800), 276 nm ($\epsilon$2,400), 236 nm ($\epsilon$6,100): $^1$H NMR (DMSO-d$_6$) δ5.85 (d, IH, J=4.5 Hz, C$_1$·H̲), 7.01 (br s, 2, NH$_2$, exchangeable in D$_2$O), 7.99 (s, 1, C$_3$H̲), 12.07 (s, 1, NH̲, exchangeable in D$_2$O). Anal. Calcd for C$_{10}$H$_{13}$N$_5$O$_4$S (299.30): C, 40.13: H, 4.38: N, 23.40: S, 10.71. Found: C, 39.88: H, 4.37: N, 23.12: S, 10.49.

6-Amino-1-β-D-ribofuranosylpyrazolo3,4-d1pyrimidine-4-sulfenamide (32)

To aqueous 5.25% sodium hypochlorite solution (4.6 mL) cooled to 0° C. was added 1.4N NH$_4$OH (12 mL) and stirred for 10 min. 6-Amino-1-β-D-ribofuranosylpyrazolo[3,4-d]pyrimidine-4-thione 31 (900 mg, 3 mmol) in 2N KOH (1.5 mL) was added and allowed to stand for 2 h at 0° C. EtOH (15 mL) was added to dissolve the gelatinous reaction mixture and filtered. The filtrate was evaporated to dryness with a small amount of silica gel. Purification of the residue on silica gel with $CH_2Cl_2$:MeOH (6:1, v/v) gave 144 mg (15%) of the title compound 32 : m.p. 145°–150° C. (dec): UV: $\lambda_{max}$ (pH 1) 327 nm ($\epsilon$6,300): 253 nm (5,200), 236 nm (10,600): $\lambda_{max}$ (pH 7) 303 nm (66,500): 273 nm (5,500) 232 nm (17,700): $\lambda_{max}$ (pH 11) 303 nm ($\epsilon$6,100): 274 nm (5,000), 232 nm (16,000): $^1$H NMR (DMSO-d$_6$): δ4.74 (s, 2, SNH$_2$, exchangeable in D$_2$O), 5.99 (d, 1, J =4.5 Hz, C$_1$·H̲)), 6.81 (s, 2, NH$_2$, exchangeable in D$_2$O) B.34 (s, 1, C$_3$H̲): Anal. Calcd for C$_{10}$H$_{14}$N$_6$O$_4$S.¼H$_2$O. (318.82): C, 37.67: H, 4.58: N, 26.36: S, 10.06. Found: C, 37.88: H, 4.58: N, 25.95: S, 9.67.

EXAMPLE 23

6-Amino-1-β-D-ribofuranosylpyrazolo[3.4-d1pyrimidine-4-sulfinamide (33)

A solution of 6-amino-1-β-D-ribofuranosylpyrazolo[3,4d]pyrimidine-4-sulfenamide (32) (100 mg, 0.32 mmol) in EtOH (40 mL) was cooled to 0° C. and m-chloroperoxybenzoic acid (85%, 70 mg, 0.34 mmol) in EtOH (20 mL) was added dropwise during 20 min. The mixture was concentrated to 5 mL in vacuo below 10° C., and then ether (30 mL) was added to yield 3 mg (69%) of desired compound 33 : m.p. 158°–162° C. (dec): UV: $\lambda_{max}$ (pH 1) 327 nm ($\epsilon$3,500): 233 (13,000): $\lambda_{max}$ (pH 7 and 11) 323 nm ($\epsilon$4,700): 232 (17,000): IR (KBr) 1065 (S=O) cm$^{-1}$: $^1$H NMR (DMSO-d$_6$) δ 6.06 (d, 1, J =5.0 Hz, C$_1$·H̲) 6.77 (s, 2, SONH$_2$, exchangeable in D$_2$O), 7.34 (br s, 2, NH$_2$, exchangeable in D$_2$O), 8.27 (d, 1, C$_3$H̲): Anal. Calcd for C$_{10}$H$_{14}$N$_6$O$_5$S.1/3H$_2$O (336.32): C, 35.71: H, 4.39: N, 24.99: S, 9.53. Found: C, 35.95: H, 4.21: N, 24.86: S, 8.93.

EXAMPLE 24

6-Amino-1-β-D-ribofuranosylimidazo[4.5-c1pyridine-4-sulfenamide (35)

Aqueous sodium hypochlorite (5.25%, 4.6 mL, 3.2 mmol) was cooled to 0° C. Twelve mL of 1.4N ammonium hydroxide was added and stirred for 10 min at 0° C. A suspension of 6-amino-1-β-D-ribofuranosylimidazo [4,5-c]pyridine-4(5H)-thione 34, prepared as per P. D. Cook and R. K. Robins, *J. Oro. Chem.*, 43, 189 (1978), (900 mg, 3 mmol) in 2N potassium hydroxide (1.5 mL) was added and stirred for 1.5 h at 0° C. The precipitate was collected by filtration, washed with water, EtOH, and acetone and dried at room temperature over P$_2$O$_5$ to yield 660 mg of desired compound 35: m.p. 134°–137° C. (dec): UV: $\lambda_{max}$ (pH 1) 374 nm ($\epsilon$7,000): 264 (5,400), 230 (21,400) $\lambda_{max}$ (pH 7) 322 nm ($\epsilon$5,500), 261 (5,800) 223 (24,000): $\lambda_{max}$ (pH 11) 319 nm ($\epsilon$8,500), 223 (24,100): $^1$H NMR (DMSO-d$_6$): δ3.70 (s, 2, exchangeable in D20, SNH$_2$), 5.61 (d, 1, J =6.4 Hz, C$_1$·H̲), 5.63 (s, 2, exchangeable in D$_2$O, NH$_2$), 6.25 (s, 1, C$_7$H̲), 8.12 (s, 1, C$_2$H̲). Anal. Calcd for C$_{11}$H$_{15}$N$_5$O$_4$S.½H$_2$O: C, 40.99: H, 5.00: N, 21.73: S, 9.95. Found: C, 41.12: H, 4.81: N, 21.43: S, 10.23.

EXAMPLE 25

6-Amino-1-β-D-ribofuranosylimidazo4,5-c1pyridine-4-sulfinamide (36)

To a solution of 6-amino-1-β-D-ribofuranosylimidazo[4,5-c]pyridine-4-sulfenamide 35 (150 mg, 0.48 mmol) in EtOH (60 mL) was added m-chloroperoxybenzoic acid (85%, 95 mg, 0.48 mmol) portionwise during 40 min at 0° C. After stirring for an additional 10 min, the mixture was filtered. The filtrate was concentrated to 10 mL and poured into ethyl ether (40 mL). The title compound was obtained as precipitate which was collected by filtration, washed with ethyl ether and dried at room temperature over $P_2O_5$ in vacuo to yield 105 mg (67%) : m.p. 171°–176° C.: UV: $\lambda_{max}$ (pH 1) 344 nm ($\epsilon$3,400), 263 (3,150), 230 (19,900) : $\lambda_{max}$ (pH 7) 317 nm ($\epsilon$3,100), 259 (2,900) 225 (19,700): $\lambda_{max}$ (pH 11) 318 nm ($\epsilon$3,200), 258 (3,000), 225 (19,900): IR (KBr): 1045 (S=O) cm$^{-1}$: $^1$H NMR (DMSO-d$_6$): δ5.71 (d, 1, J =6.1 Hz, C$_1$·H ), 6.03 (s, 2, SONH$_2$, exchangeable in D$_2$O), δ6.33 (s, 2, NH$_2$, exchangeable in D$_2$O), δ6.68 (s, IH, C$_7$H), 8.36 (s, 1, C$_2$H). Anal. Calcd for C$_{11}$H$_{15}$N$_5$O$_5$S.½H$_2$O: (338.34): C, 39.05: H, 4.77: N, 20.69: S, 9.48. Found: C, 39.43: H, 4.56: N, 0.29: S, 9.43.

EXAMPLE 26

2-Amino-7-(2-deoxy-β-D-erythro-pentofuranosyl)pyrrolo[2,3-d]pyrimidine-4-sulfenamide (38)

Four mL of 5.25% aqueous sodium hypochlorite (2.8 mmol) was cooled and added to 10 mL of 1.4N ammonium hydroxide. After stirring for 30 min at 0° C., 2-amino-7-(2-deoxy-β-D-erythro-pentofuranosyl) pyrrolo[2,3-d]pyrimidine-4-thione 37 (0.78 g, 2.8 mmol) in 1.3 mL of 2N potassium hydroxide was added and stirred for 1 h at 0° C. The precipitate was collected by filtration, washed with EtOH and dried at 25° C. over P$_2$O$_5$ in vacuo to obtain 670 mg (81%) of the title compound 38. m.p. 162°–164° C. (dec): UV: $\lambda_{max}$ (pH 1) 238 nm ($\epsilon$28,500): 347 (5,600): $\lambda_{max}$ (pH 7) 234 nm ($\epsilon$35,400), 317 (10,400): $\lambda_{max}$ (pH 11) 234 nm ($\epsilon$30,900), 318 (10,300): $^1$H NMR (DMSO-d$_6$): δ4.11 (s, 2, exchangeable in D$_2$O, SNH$_2$), 6.18 (s, 2, exchangeable in D$_2$O, NH$_2$), 6.44 (dd, 1, J =8.3 and 5.9 Hz, C$_1$·H), 6.61 (d, 1, J =3.8 Hz, C$_5$H), 6.18 (d, 1, J =3.8 Hz, C$_6$H). Anal. Calcd for C$_{11}$H$_{15}$N$_5$O$_3$S.¼H$_2$O: (301.83): C, 43.77: H, 5.17: N, 23.20: S, 10.62. Found: C, 43.59: H, 4.95: N, 23.13: S, 10.32.

EXAMPLE 27

2-Amino-7-(2-deoxy-β-D-erythro-pentofuranosyl)pyrrolo-[2,3-d]pyrimidine-4-sulfinamide (39)

2-Amino-7-(2-deoxy-β-D-erythro-pentofuranosyl)-pyrrolo[2,3-d1pyrimidine-4-sulfenamide 38 (300 mg, 1 mmol) was suspended in EtOH (120 mL) and cooled to 0° C. m-Chloroperoxybenzoic acid (85%, 100 mg, 1 mmol) in EtOH (30 mL) was added dropwise during 1.5 h. After stirring for an additional 30 min at 0° C., the mixture was concentrated to 10 mL in vacuo below 25° C. Ethyl ether (100 mL) was added to the concentrate solution and allowed to stand in the refrigerator overnight. The precipitate was collected by filtration, washed with ethyl ether and dried at 25° C. under reduced pressure to yield 110 mg (35%) of desired compound 39: m.p. 122 C (dec): UV: $\lambda_{max}$ (pH 1) 352 nm ($\epsilon$3,100), 272 (3,100), 240 (21,100): $\lambda_{max}$ (pH 7) 336 nm ($\epsilon$4,800), 239 (21,500): $\lambda_{max}$ (pH 11) 337 nm ($\epsilon$4,600), 239 (20,500): IR (KBr) 1060 (S=O) cm$^{-1}$:$^1$H NMR (DMSO-d$_6$): δ6.45 (s, 2, exchangeable in D$_2$O, SONH$_2$), 6.49, (dd, 1, J =8.3 and 5.9 Hz, C$_1$·H), 6.62 (s, 2, exchangeable in D$_2$O, NH$_2$), 6.73 (d, 1, J 3.8 Hz, C$_5$H), 7.38 (d, 1, J =3.8 Hz, C$_6$H). Anal. Calcd for C$_{11}$H$_{15}$N$_5$O$_4$S: C, 42.16: H, 4.82: N, 22.35: S, 10.23. Found: C, 41.91: H, 4.86: N, 22.07: S, 9.91.

EXAMPLE 28

2-Amino-9-(5-deoxy-β-D-ribofuranosyl)-9H-purine-6-sulfenamide (41)

Commercial 0.77M sodium hypochlorite (5.25%, 3.2 mL) was cooled to <0° C. in an ice-salt bath and added with stirring to similarly cooled 1.4M ammonium hydroxide (29%, 0.8 mL diluted to 8 mL with water). The resulting solution of the chloramine was mixed with a solution of 2-amino-9-(5-deoxy-β-D-ribofuranosyl)-9H-6-thiopurine [E. J. Reist, P. A. Hart, L. Goodman and B. R. Baker, *J. Oro. Chem.*, 26, 1557 (1961), 40, 0.56 g, 2 mmol]] in 2M potassium hydroxide solution (1 mL) at 0° C. The mixture was stirred until it had warmed to room temperature ($\approx$2 h). After 3 h of stirring, the clear reaction mixture was evaporated to dryness. The residue was dissolved in methanol (20 mL), adsorbed onto silica gel ($\approx$2 g) and the excess solvent evaporated under reduced pressure The dry residue was loaded onto a silica gel column (1.5×20 cm) packed in dichloromethane. The column was eluted with dichloromethane:methanol (85:15, 8:2, v/v). The appropriate homogeneous fractions were pooled and the solvent evaporated to yield 0.52 g (87%) of 41, mp 160°–162° C (dec.): UV $\lambda_{max}$ (pH 1) 328 nm ($\epsilon$ 10,800): $\lambda_{max}$ (pH 7) 306 nm ($\epsilon$ 9,500): $\lambda_{max}$ (pH 11) 308 nm ($\epsilon$ 10,300): $^1$H NMR (DMSO-d$_6$): δ 1.28 (d, 3, CH$_3$), 3.89 (s, 2, SNH$_2$, exchanged with D$_2$O), 5.74 (d, 1, J=5.22 Hz, C$_1$·H), 6.51 (s, 2, NH$_2$, exchanged with D$_2$O), 8.12 (s, 1, C$_8$e-,uns/H/ ), and other sugar protons. Anal. Calcd. for C$_{10}$H$_{14}$N$_6$O$_3$S (298.32): C, 40.26; H, 4.73; N, 28.17; S, 10.75. Found: C, 40.49; H, 5.0I; N, 27.85; S, 10.56.

EXAMPLE 29

2-Amino-9-(5-deoxy-β-D-ribofuranosyl)-9H-purine-6-sulfinamide (42)

A solution of m-chloroperoxybenzoic acid (0.10 g, 0.5 mmol) in ethanol (10 mL) was added dropwise to an ice-cooled stirred solution of 41 (0.15 g, 0.5 mmol) in ethanol (25 mL), during 15 min. The reaction mixture was allowed to stand at 0° C. overnight and then evaporated to dryness under reduced pressure. The residue was triturated with a mixture of ethanol (2 mL) and ethyl ether (30 mL). The precipitated crystalline product was collected by filtration and dried at 80° C. for 3 h to yield 70 mg (45%) of the title compound, mp >100° C. (dec.). IR (KBr): 1050 (vs, s, S=O), 3100–3600 (NH$_2$, OH)cm$^{-1}$:UV: $\lambda_{max}$ (pH 1) 330 nm ($\epsilon$ 3,600): $\lambda_{max}$ (pH 7) 324 nm ( 4,400): $\lambda_{max}$ (pH 11) 321 nm 4,300): $^1$H NMR (DMSO-d$_6$): δ 1.30 (d, 3, CH$_3$), 5.80 (d, 1, J 5.25 Hz, C$_1$·H), 6.51 (s, 2, SONH$_2$, exchanged with D$_2$O), 6.98 (s, 2, NH$_2$, exchanged with D$_2$O), 8.40 (s, 1, C$_8$H), and other sugar protons. Anal. Calcd. for C$_{10}$H$_{14}$N$_6$O$_4$S (314.32): C, 38.21; H, 4 49; N, 26.74; S, 10.20. Found: C, 37.98; H, 4.41; N, 26.51; S, 9.91.

EXAMPLE 30

2-Amino-9-(5-deoxy-β-D-ribofuranosyl)-9H-purine-6-sulfonamide (43)

To a stirred solution of 41 (0.30 g, 1 mmol) in ethanol (35 mL) at room temperature was added m-chloroperoxybenzoic acid (0.80 g, 4 mmol) and the mixture was allowed to stand overnight. The reaction mixture was evaporated to dryness and the residue was triturated with a mixture of ethanol (2 mL) and ethyl ether (20 mL). After storing in the refrigerator ($\approx 4°$ C.) overnight, the precipitated crystalline product was collected by filtration and dried at 80° C. for several hours to yield 0.17 g (52%) of the title compound, mp $>90°$ C. IR (KBr): 1160 (s, S=O), 1350 (vs, b, SO$_2$), 3000–3600 (NH$_2$, OH)cm$^{-1}$; UV: $\lambda_{max}$ (pH 1) 331 nm ($\epsilon$ 5,400): $\lambda_{max}$ (pH 7) 326 nm ($\epsilon$ 5,500): $\lambda_{max}$ (pH 11) 318 (6 6,500): 1H NMR (DMSO-d$_6$): δ 1.30 (d, 3, CH3), 5.80 (d, 1, J =5.13 Hz, C$_1\cdot$H), 6.99 (s, 2, SO$_2$NH$_2$, exchanged with D$_2$O), 7.54 (s, 2, NH$_2$, exchanged with D$_2$O), 8.44 (s, 1, C$_8$e,uns/H/ ), and other sugar protons. Anal. Calcd. for C$_{10}$H$_{14}$N$_6$O$_5$S (330.32): C, 36.36; H, 4.27; N, 25.45; S, 9.71. Found: C, 36.41; H, 4.55; N, 25.38; S, 10.08.

EXAMPLE 31

2-Amino-9-(2-deoxy-β-D-erythro-pentofuranosyl)-9H-purine-6-sulfenamide (45)

Commercial 0.77M sodium hypochlorite (5.25%, 15 mL) was cooled to $<0°$ C. in an ice-salt bath and added with stirring to similarly cooled 1.4M ammonium hydroxide (29%, 3.7 mL diluted to 40 mL with water). The resulting solution of the chloramine was mixed with a solution of 2-amino-9-(2-deoxy-α-D-erythro-pentofuranosyl)-9H-6-thiopurine [R. H. Iwamoto, E. M. Acton and L. Goodman, J. Med. Chem., 6, 684 (1963), 44, 2.83 g, 10 mmol] in 2M potassium hydroxide solution (5 mL) at 0° C. The reaction mixture was stirred until it had warmed to room temperature (about an hour). The crystalline material that deposited was collected by filtration, washed with cold water (2×5 mL), followed by ethanol (10 mL) and air-dried to yield 2.5 g (84%) of the title compound, mp 163° C. (dec.): UV: $\lambda_{max}$ (pH 1) 328 nm ($\epsilon$ 9,700): $\lambda_{max}$ (pH 7) 308 nm ($\epsilon$ 11,900): $\lambda_{max}$ (pH 11) 308 nm ($\epsilon$ 12,400): 1H NMR (DMSO-d$_6$): 3 98 (s, 2, SNH$_2$, exchanged with D$_2$O), 6.21 (dd, 1, J =5.10 Hz, C$_1\cdot$H), 6.49 (s, 2, NH$_2$, exchanged with D$_2$O), 8.19 (s, 1, C$_8$e,uns/H/ ), and other sugar protons. Anal. Calcd. for C$_{10}$H$_{14}$N$_6$O$_3$S (298.32): C, 40.27; H, 4.70; N, 28.19; S, 10.74. Found: C, 39.98; H, 4.70; N, 28.01; S, 10.79.

EXAMPLE 32

2-Amino-9-(2-deoxy-β-D-erythro-pentofuranosyl)-9H-purine-6-sulfinamide (46)

A solution of m-chloroperoxybenzoic acid (0.50 g, 2.5 mmol) in ethanol (50 mL) was added dropwise to an ice-cooled (0°–5° C.), stirred solution of 45 (0.75 g, 2.5 mmol) in ethanol (150 mL), during 15 min. The reaction mixture was allowed to stand at room temperature overnight and the crystalline product that deposited was collected by filtration. The product was washed with ethanol (2×15 mL) and air-dried to yield 0.24 g (31%) of 46. mp 178° C. (dec.). IR (KBr): 1040, 1300 (s, S=O), 3100–3600 (NH$_2$, OH)cm$^{-1}$; UV: $\lambda_{max}$ (pH 1) 329 nm ($\epsilon$ 3,800); $\lambda_{max}$ (pH 7) 323 nm ($\epsilon$ 5,800): $\lambda_{max}$ (pH 11) 323 nm ($\epsilon$ 3,700): 1H NMR (DMSO-d$_6$): δ 6.27 (dd, 1, J=5.5 Hz, C$_1\cdot$H), 6.50 (s, 2, SONH$_2$, exchanged with D$_2$O), 6.94 (s, 2, NH$_2$, exchanged with D$_2$O), 8.43 (s, 1, C$_8$H), and other sugar protons. Anal. Calcd. for C$_{10}$H$_{14}$N$_6$O$_4$S (314.32): C, 38.21; H, 4.49; N, 26.74; S, 10.20. Found: C, 38.34; H, 4.59; N, 26.47; S, 10.17.

EXAMPLE 33

2-Amino-9-(2-deoxy-o-D-erythro-pentofuranosyl)-9H-purine-6-sulfonamide (47)

To a stirred solution of 45 (0.75 g, 2.5 mmol) in ethanol (150 mL) at room temperature was added m-chloroperoxybenzoic acid (2.0 g, 10 mmol) and the mixture was stirred for 3 h. Silica gel ($\approx 2$ g) was added to the clear reaction mixture and the excess solvent was evaporated under reduced pressure. The dry residue was loaded onto a silica gel column (1.5×20 cm) packed in dichloromethane. The column was eluted with dichloromethane:methanol (85:15, 8:2, v/v). The appropriate homogeneous fractions were pooled and the solvent evaporated to dryness. The residue was crystallized from aqueous ethanol to yield 0.30 g (36%) of the title compound, mp $>100°$ C. IR (KBr): 1160, 1340 (vs, SO$_2$), 3000–3600 (NH$_2$, OH)cm$^{-1}$:$\lambda_{max}$ (pH 1) 333 nm ($\epsilon$ 5,800): $\lambda_{max}$ (pH 7) 327 nm ($\epsilon$ 9,800): $\lambda_{max}$ (pH 11) 319 nm ($\epsilon$ 10,500): 1H NMR (DMSO-d$_6$): δ 6.27 (dd, 1, J=5.37 Hz, C$_1\cdot$H), 6.96 (s, 2, SO$_2$NH$_2$, exchanged with D$_2$O), 7.51 (s, 2, NH$_2$, exchanged with D$_2$O), 8.46 (s, 1, C$_8$e,uns/H/ ), and other sugar protons. Anal. Calcd. for C$_{10}$H$_{14}$N$_6$O$_5$S (330.32): C, 36.36; H, 4.27; N, 25.45; S, 9.71. Found: C, 36.11; H, 4.25; N, 25.31; S, 10.08.

EXAMPLE 34

2-Amino-9-β-D-arabinofuranosyl-9H-purine-6-sulfenamide (49)

To an ice-cold solution of ammonium hydroxide (1.4N, 20 mL) was added 0.77M sodium hypochlorite solution (5.25%, 7.5 mL, 5.25 mmol) in one lot. The mixture was stirred at 0° C. for 10 min. A solution of 2-amino-9-β-D-arabinofuranosyl-9H-purine-6-thione [W. W. Lee, A. P. Martinez, R. W. Blackford, V. J. Bartuska, E. J. Reist and L. Goodman, J. Med. Chem., 14, 819 (1971), 48. 1.49 g, 5 mmol] in 1N potassium hydroxide solution (5 mL, 5 mmol) was added in one lot, and the reaction mixture was stirred at 0° C. for 1 h. After allowing the reaction mixture to warm up to 15° C. during 1 h, the clear solution was evaporated to dryness under reduced pressure. The residue was purified by flash chromatography over silica gel using dichloromethane→methanol gradient. The homogeneous fractions were pooled and evaporated to dryness. The residue was crystallized from a mixture of dichloromethane and methanol to give 0.85 g (54%) of the title compound, mp 190°–192° C. IR (KBr): 3200–3400 (NH$_2$, OH)cm$^{-1}$:UV: $\lambda_{max}$ (pH 1) 227 nm ($\epsilon$ 26,400), 254 (10,600), 328 (19,400): $\lambda_{max}$ (pH 7) 222 nm ($\epsilon$ 22,200), 243 (13,700), 308 (13,200): $\lambda_{max}$ (pH 11) 221 nm ($\epsilon$ 22,200), 243 (13,500), 308 (13,200): 1H NMR (DMSO-d$_6$) 4.09 (s, 2, SNH$_2$, exchanged with D$_2$O), 6.13 (d, 1, J =4.0 Hz, C$_1\cdot$H), 6.50 (s, 2, NH$_2$, exchanged with D$_2$O), 7.99 (s, 1, C$_8$e,uns/H/ ), and other sugar protons. Anal. Calcd. for ClOH$_{14}$N$_6$O$_4$S (314.32): C, 38.21; H, 4.49; N, 26.74; S, 10.20. Found: C, 38.40; H, 4.47; N, 26.53; S, 10.29.

EXAMPLE 35

2-Amino-9-β-D-arabinofuranosyl-9H-purine-6-sulfinamide (50)

A solution of 49 (1.5 g, 4.7 mmol) in ethanol (350 mL) and water (50 mL) was cooled to 0° C. To this cold solution was added m-chloroperoxybenzoic acid (80%, 0.90 g, 4.45 mmol) in ethanol (50 mL) during 1.5 h. After the addition, the reaction mixture was stirred at ice-bath temperature for 1.5 h. The solvent was evaporated under reduced pressure and the residue was dissolved in methanol (50 mL). Silica gel ($\approx 5$ g) was added and evaporated to dryness. The dried silica gel was placed on top of a flash silica gel column and the column was eluted with ethyl acetate→methanol gradient. The pure compound crystallized out after concentration of the homogeneous fractions. The product was collected by filtration and dried to give 0.95 g (60%) of the title compound, mp >200° C. (dec.): IR (KBr): 1120 (S=O), 3100–3600 (NH$_2$, OH)cm$^{-1}$: UV: $\lambda_{max}$ (pH 1) 220 nm ($\epsilon$17,900), 249 (7,600), 330 (5,100): $\lambda_{max}$ (pH 7) 225 nm ($\epsilon$24,100), 248 (sh) (6,100), 323 (8,000): $\lambda_{max}$ (pH 11) 224 nm ($\epsilon$ 21,000), 244 (sh) (6,600), 322 (6,600): $^1$H NMR (DMSO-d$_6$): δ 6.17 (d, J 4.08 Hz, C$_1$H), 6.50 (s, 2, SONH$_2$, exchanged with D$_2$O), 6.97 (s, 2, NH$_2$, exchanged with D$_2$O), 8.25 (s, 1, C$_8$H), and other sugar protons. Anal. Calcd. for C$_{10}$H$_{14}$N$_6$O$_5$S (330.32): C, 36.36; H, 4.27; N, 25.44; S, 9.71. Found: C, 36.65; H, 4.09; N, 25.19; S, 9.56.

EXAMPLE 36

2-Amino-9-β-D-arabinofuranosyl-9H-purine-6-sulfonamide (51)

To a stirred solution of 49 (0.46 g, 1.46 mmol) in ethanol (250 mL) and water (50 mL) was added m-chloroperoxybenzoic acid (1.0 g, 5.84 mmol) in ethanol (50 mL) dropwise during 1 h at room temperature. After the addition, the reaction mixture was stirred at room temperature for 6 h and evaporated to dryness under reduced pressure. The residue was purified by flash silica gel chromatography using ethyl acetate→methanol as the gradient. The homogeneous fractions were pooled and evaporated to dryness to give 0.30 g (59%) of the title compound, mp >193° C. IR (KBr): 1170 (S=O), 1340 (SO$_2$), 3100–3600 (NH$_2$, OH)cm$^{-1}$: UV: $\lambda_{max}$ (pH 1) 222 nm ($\epsilon$ 16,900), 332 (4,200): $\lambda_{max}$ (pH 7) 225 nm 17,300), 326 (4,900): $\lambda_{max}$ (pH 11) 223 nm ($\epsilon$ 17,200), 320 (5,600): $^1$H NMR (DMSO-d$_6$): δ 6.18 (d, 1, J =4.3 Hz, C$_1$H), 6.95 (s, 2, SO$_2$NH$_2$, exchanged with D$_2$O), 7.48 (br s, 2, NH$_2$, exchanged with D$_2$O), 8.27 (s, 1, C$_8$H), and other sugar protons. Anal. Calcd. for C$_{10}$H$_{14}$N$_6$O$_6$S·½EtOAc (390.37): C, 36.92; H, 4.65; N, 21.52; S, 8.20. Found: C, 37.04; H, 4.32; N, 21.50; S, 8.41.

EXAMPLE 37

7-(2-Deoxy-β-D-erythro-pentofuranosyl)pyrrolo2,3-d1-pyrimidine-4-sulfenamide (53).

To an ice-cold solution of ammonium hydroxide (1.4N, 8 mL) was added 0.77M sodium hypochlorite solution (5.25%, 3 mL, 2.1 mmol) in one lot. The mixture was stirred at 0° C. for 10 min. A solution of 7-(2-deoxy-β-D-erythropentofuranosyl)pyrrolo[2,3-d]pyrimidine-4-thione [H. B. Cottam, Z. Kazimierczuk, S. Geary, P. A. McKernan, G. R. Revankar and R. K. Robins, *J. Med. Chem.*, 28, 1461 (1985), 52, 0.53 g, 2 mmol] in 1N potassium hydroxide solution (2 mL, 2 mmol) was added in one lot, and the reaction mixture was stirred at 0° C. for 1 h. After allowing the reaction mixture to warm up to 15° C. during 1 h, the clear solution was evaporated to dryness under reduced pressure. The residue was purified by flash chromatography over silica gel using dichloromethane:methanol (95:5, v/v) as the eluent. The homogeneous fractions were pooled and evaporated to dryness. The residue was crystallized from a mixture of methanol and dichloromethane to give 0.31 g (55%) of the title compound, mp 153°–155° C. IR (KB)): 3200–3450 (NH$_2$, OH)cm$^{-1}$:UV: $\lambda_{max}$(pH 1) 266 nm 9,900), 321 (22,900): $\lambda_{max}$(pH 7) 295 nm 11,200): $\lambda_{max}$ (pH 11) 306 nm ($\epsilon$17,100): $^1$H NMR (DMSO-d$_6$): δ 4.29 (s, 2, SNH$_2$, exchanged with D$_2$O), 6.62 (t, 1, J =6.7 Hz, C$_1$H), 6.85 (d, 1, C$_5$H), 7.71 (d, 1, C$_6$H), 8.54 (s, 1, C$_2$H), and other sugar protons. Anal. Calcd. for C$_{11}$H$_{14}$N$_4$O$_3$S (282.28): C, 46.80; H, 4.99; N, 19.84; S, 11.34. Found: C, 47.01; H, 4.63; N, 19.63; S, 11.52.

EXAMPLE 38

7-(2-Deoxy-β-D-erythro-pentofuranosyl)pyrrolo[2,3-d1-pyrimidine-4-sulfinamide (54)

To a solution of 53 (1.41 g, 5 mmol) in ethanol:water (190:10, v/v), cooled to 0° C. in an ice bath was added m-chloroperoxybenzoic acid (80%, 1.01 g, 5 mmol) in ethanol (50 mL), dropwise during 1.5 h. The reaction mixture was stirred at 0° C. for 1.5 h before the solvent was evaporated under reduced pressure. The residue was dissolved in ethanol (25 mL) and diluted with ethyl ether (150 mL) and stored in the refrigerator overnight. The precipitated solid was collected by filtration and dried to yield 1.0 g (67%) of the title compound, mp 170°–172° C. IR(KBr): 1100 (S=O), 3200–3400 (NH$_2$, OH)cm$^{-1}$; UV: $\lambda_{max}$ (pH 1) 231 nm ($\epsilon$30,300), 273 (6,200): $\lambda_{max}$ (pH 7): 227 nm ($\epsilon$ 28,300), 285 (6,200), 302 (sh) (5,400): $\lambda_{max}$(pH 11): 224 nm ($\epsilon$ 22,800), 273 (5,900), 301 (sh) (3,200): $^1$H NMR (DMSO-d$_6$): δ 6.66 (s, 2, SONH$_2$, exchanged with D$_2$O), 6.71 (t, 1, J 6.8 Hz, C$_1$H), 7.06 (d, 1, C$_5$H), 7.97 (d, 1, C$_6$H), 8.86 (s, 1, C$_2$H), and other sugar protons. Anal. Calcd. for C$_{11}$H$_{14}$N$_4$O$_4$S (298.28): C, 44.29; H, 4.73; N, 18.77; S, 10.73. Found: C, 44.30; H, 4.49; N, 48.48; S, 10.91.

EXAMPLE 39

7-(2-Deoxy-β-D-erythro-pentofuranosyl)pyrrolo[2,3-d]-pyrimidine-4-sulfonamide (55)

To a stirred solution of 53 (1.41 g, 5 mmol) in a mixture of ethanol:water (300:50, v/v) was added m-chloroperoxybenzoic acid (3.44 g, 20 mmol) in ethanol (50 mL) dropwise during 1.5 h at room temperature. After the addition, the reaction mixture was stirred at room temperature for 12 h and evaporated to dryness under reduced pressure. The residue was dissolved in ethanol (50 mL), mixed with silica gel ($\approx 5$ g) and again evaporated to dryness in vacuo. The dry residue was placed on top of a flash silica gel column (5×30 cm). The column was eluted successively with dichloromethane (1L), dichloromethane:acetone (1:1, 500 mL) and then dichloromethane→methanol gradient. The appropriate homogeneous fractions were pooled and concentrated to about 50 mL, and stored in the refrigerator overnight. The product that crystallized out was collected by filtration and dried to yield 1.10 g (71%), mp 175°–177° C. IR (KBr): 1150 (S=O), 1350 (SO$_2$), 3100–3600 (NH$_2$, OH)cm$^{-1}$: UV: $\lambda_{max}$(pH 1) 228 nm ($\epsilon$ 27,700), 284 (5,100), 310 (sh) (3,800): $\lambda_{max}$(pH 7) 228 nm ($\epsilon$ 27,400), 285 (4,900), 308 (sh) (3,800): $\lambda_{max}$(pH 11) 226 nm ($\epsilon$ 25,800), 284 (5,700): $^1$H NMR (DMSO-d$_6$): $\delta$ 6.72 (t, 1, J =7.2 Hz, C$_1$'H), 6.92 (d, 1, C$_5$H), 7.82 (br s, 2, SO$_2$NH$_2$, exchanged with D$_2$O), 8.08 (d, 1, C$_6$H), 8.96 (s, 1, C$_2$H), and other sugar protons. Anal. Calcd. for C$_{11}$H$_{14}$N$_4$O$_5$S (314.22): C, 42.04; H, 4.49; N, 17.82; S, 10.18. Found: C, 42.07; H, 4.46; N, 17.62; S, 10.15.

EXAMPLE 40

1-$\beta$-D-Ribofuranosylpyrazolo3,4-d1pyrimidine-4-sulfenamide (57)

Commercial 0.77M sodium hypochlorite (5.25%, 8 mL) was cooled to <0° C. in an ice-salt bath and added with stirring to a similarly cooled 0.7M ammonium hydroxide (29%, 2 mL diluted to 20 mL with water). The resulting solution of chloramine was mixed with a solution of 1-$\beta$-D-ribofuranosylpyrazolo [3,4-d]pyrimidine-4(5H)-thione [J. L. G. Montero, G. A. Bhat, R. P. Panzica and L. B. Townsend, *J. Heterocycl. Chem.*, 14, 483 (1977), 56. 1.42 g, 5 mmol] in 2M potassium hydroxide solution (2.5 mL) at 0° C. The reaction mixture was stirred until it had warmed to room temperature (about an hour), and allowed to stand for 2 more hours. The product that crystallized out was collected by filtration, washed with cold ethanol (2×10 mL) and dried at room temperature to yield 0.61 g (41%) of the title compound. Recrystallization from ethanol:water (3:1) gave analytically pure material of mp 166°–169° C. UV: $\lambda_{max}$ (pH 1) 295 nm ($\epsilon$28,000): $\lambda_{max}$ (pH 7) 293 nm ($\epsilon$ 24,000): $\lambda_{max}$ (pH 11) 292 nm ($\epsilon$ 21,000): $^1$H NMR (DMSO-d$_6$): $\delta$ 4.70 (s, 2, SNH$_2$, exchanged with D$_2$O), 6.24 (d, 1, J =4.53 HZ, C$_1$'H), 8.67 (s, 1, C$_3$H), 8.75 (s, 1, C$_6$H), and other sugar protons. Anal. Calcd. for C$_{10}$H$_{13}$N$_5$O$_4$S (299.3): C, 40.13; H, 4.38; N, 23.40; S, 10.71. Found: C, 40.35; H, 4.34; N, 23.28; S, 10.79.

EXAMPLE 41

2-Amino-9-(2,3,5-tri-0-acetyl-$\beta$-D-ribofuranosyl)-9H-purine-6-sulfinamide (58)

A mixture of dimethylaminopyridine (10 mg) and acetic anhydride (1 mL) in anhydrous N,N-dimethylformamide (2 mL) was cooled to −15° C. 2-Amino-9-$\beta$-D-ribofuranosyl-9H-purine-6-sulfinamide (19, 0.10 g, 0.3 mmol) was added and the mixture was stirred for 40 min at −15° C. The reaction was quenched by the addition of methanol (4 mL) and the resulting solution was stirred at −10° C. for 20 min and then evaporated to dryness. The residue was triturated with ethyl ether (10 mL) and the product was precipitated by the addition of hexane to yield 0.102 g (75%) of the title compound as amorphous solid. IR (KBr): 1050, 1095 (s, S=O), 1745 (vs, C=O), 3200–3500 (NH$_2$)cm$^{-1}$:UV: $\lambda_{max}$ (pH 1) 335 nm ($\epsilon$ 6,100): $\lambda_{max}$ (pH 7) 328 nm ($\epsilon$ 6,700): $\lambda_{max}$ (pH 11) 321 nm 7,000): $^1$H NMR (DMSO-d$_6$): $\delta$ 6 2.03–2.13 (3s, 9, 3COCH$_3$), 6.15 (d, 1, J =3.5 Hz, C$_1$'H), 6.51 (s, 2, SONH$_2$, exchanged with D$_2$O), 7.07 (s, 2, NH$_2$, exchanged with D$_2$O), 8.44 (s, 1, C$_8$H), and other sugar protons. Anal. Calcd. for C$_{16}$H$_{20}$N$_6$O$_8$S (456.43): C, 42,10; H, 4.42; N, 18.41; S, 7.03. Found: C, 41.99; H, 4.47; N, 18.19; S, 6.79.

As illustrative examples of use of the compounds of the invention the following examples are given. In these examples the efficacy of the compounds of the invention are demonstrated using standard tests against certain malignant tumors. These standard tests utilize protocols developed under the auspices of the Developmental Therapeutics Program, Division of Cancer Treatment, National Cancer Institute, Bethesda, Md., U.S.A. Except as otherwise indicated the tests conform to these protocols and are evaluated utilizing criteria defined by the protocols.

For the purposes of these examples certain of standard abbreviations are utilized as follows: ip—intraperitoneal: qd—Once a Day: bid—Twice a Day: tid—Three Times a Day: qid—Four Times a Day: %T/C—Percent Treated Divided by Control: %ILS—Percent Increased Life Span: inj—Injection.

For those tests whose results are indicated as % T/C generally using NCI protocols for the L1210 tumor cell line, a value greater than 125% is considered as having activity. For those tests expressed as a percent of the original inoculum, values above 100 are considered inactive while those below 100 are viewed as active. Values below 25% are considered capable of producing effective therapy, those below 10% are considered good and those below 5% are considered very good. This expresses the percent of the cells which survived treatment based upon the original cells in the inoculum. Those tests expressed as increases in life span (% ILS) indicate the increased life span of the drug treated group compared to a control group.

THERAPEUTIC EXAMPLE A

As an indicator of reproducible activity, compounds of the invention and other known cancer chemotherapeutic agents were screened against L1210 lymphoid leukemia in vivo utilizing the mouse as a test species. Normal NCI protocols for this test require $10^5$ seed cells of the L1210 cell line. However for the purposes of tests with the L1210 cell line in testing the compounds of the invention for antitumor activity, a log greater, i.e. $10^6$ cells were utilized.

Table 1 demonstrates the results of inoculating mice with $10^6$ L1210 seed cells and the spread of this tumor cell line throughout the body to multiple organ systems in the test species. As is indicative of Table 1, at day 7 the L1210 cellular population in multiple organ systems greatly exceeded $10^5$ cells in each of the organs assayed. It is thus evident from Table 1 that if a chemotherapeutic agent is to be effective against the L1210 tumor line seeded at $10^6$ it must reach all of the organ systems of the animal in view of spread of this neoplastic disease to all these organ systems.

TABLE 1

| VIABLE L1210 CELLS IN TISSUES OF BDF MICE AFTER INTRAPERITONEAL INOCULATION ON DAY 0[1] | | |
|---|---|---|
| | POST INOCULATION DAY | |
| TISSUE | 1 | 7 |
| BRAIN | <100 | >400,000 |
| LUNG | <100 | >600,000 |
| SPLEEN | >6,000 | <4,000,000 |
| LIVER | >64,000 | >120,000,000 |
| BLOOD | NONE | >300,000 |
| MARROW | NONE | >500,000 |

[1]Inoculated IP on day 0 with $10^6$ L1210 cells.

THERAPEUTIC EXAMPLE B

Tables 2-a and 2-b illustrate a dose response for Compound 19 against L1210 inoculated mice expressed as both increased life span compared to control and as the number of cells of the original inoculum surviving drug treatment. As is evident from the various regimens of drug treatment shown in Tables 2-a and 2-b, effective therapeutic effects are noted and a dose response to Compound 19 is evident. The efficacy for Compound 19 seen in Tables 2-a and 2-b is similar to that seen for Cytosine Arabinoside with the exception that to see effects with Cytosine Arabinoside like those in Tables 2-a and 2-b for compound 19. Cytosine Arabinoside must be given every three hours. Test results are given utilizing standard protocols based on mean survival time and are expressed as T/C percentages (treated animals/control animals).

TABLE 2-a

LIFE SPAN (% T/C OF L1210 INOCULATED[1] MICE TREATED[2] WITH COMPOUND 19

| DOSAGE | SCHEDULE OF DELIVERY | | | | | |
|---|---|---|---|---|---|---|
| | (qd days indicated) | | | (bid days indicated) | | |
| (mg/kg/inj) | 1,4,7 | 1,3,5,7 | 1-7 | 1,4,7 | 1,3,5,7 | 1-7 |
| 22 | — | — | — | 161 | 193 | 200 |
| 37 | 154 | 174 | 213 | 216 | 236 | 233 |
| 62 | 193 | 223 | 239 | 249 | 285 | 361[3] |
| 104 | 230 | 236 | 307[4] | 311[5] | — | — |
| 173 | 269 | 289 | — | — | — | — |

[1]BDF$_1$ female mice were inoculated ip on day 0 with 10[6] L1210 cells.
[2]Drug was delivered by the ip route.
[3]Treatment group included 2 long term survivors which were not included in the calculation of life span.
[4]Treatment group included 1 long term survivor which was not included in the calculation of life span.
[5]Treatment group included 1 mouse which died from drug toxicity and was not included in the calculation of life span.

TABLE 2-b

L1210 CELLS SURVIVING DAY 7 TREATMENT WITH COMPOUND 19 (expressed as % of original inoculum)

| DOSAGE | DRUG DELIVERED (qd days indicated) | | | DRUG DELIVERED (bid days indicated) | | |
|---|---|---|---|---|---|---|
| (mg/kg) | 1,4,7 | 1,3,5,7 | 1-7 | 1,4,7 | 1,3,5,7 | 1-7 |
| 22 | — | — | — | 9211 | 594 | 343 |
| 37 | 15936 | 3077 | 115 | 87 | 17 | 22 |
| 62 | 594 | 50 | 13 | 5.6 | 0.3 | 2/5C[1] |
| 104 | 29 | 17 | 1/5C[1] | 1/5T[2] | — | — |
| 173 | 1.1 | 0.2 | — | — | — | — |

[1]Data expressed as number of long term survivors (Cures) per the number of animals in test group.
[2]Data expressed as number of toxic deaths (Toxic Doses) per the number of animals in test group.

THERAPEUTIC EXAMPLE C

In Example C the oral efficacy of Compound 19 was compared to that for the drug when given intraperitoneally.

TABLE 3

RESPONSES OF L1210-INOCULATED BDF$_1$ MICE TO COMPOUND 19 GIVEN ORALLY AND INTRAPERITONEALLY

| DRUG DOSAGE | INCREASED LIFE SPAN PRODUCED BY COMPOUND 19 DELIVERED | |
|---|---|---|
| (MG/KG/INJ) | ORALLY | INTRAPERITONEALLY |
| 37 | 45 | 54 |
| 62 | 45 | 93 |
| 104 | 38 | 130 |
| 173 | 38 | 169 |

Mice were inoculated intraperitoneally on day 0 with a million cells of murine leukemia L1210. Drug was given qd days 1, 4 and 7. Increased life span is the mean increase in the treated group presented as a percentage of the mean life span of control mice.

THERAPEUTIC EXAMPLE D

In Example D compound 19 is compared with 6-Thioguanosine. As per the oral treatment of Compound 19 seen in Table 3, in Table 4 it is evident that Thioguanosine has a flat dose response whereas Compound 19 shows a dose response curve when injected intraperitoneally.

TABLE 4

RESPONSES OF L1210-INOCULATED BDF$_1$ MICE TO TREATMENT WITH 6-THIOGUANOSINE OR COMPOUND 19

| DRUG DOSAGE | INCREASED LIFE SPAN PRODUCED BY | |
|---|---|---|
| (MG/KG/INJ) | 6-THIOGUANOSINE | COMPOUND 19 |
| 8.1 | 48 | NR |
| 13 | 38 | NR |
| 22 | 42 | NR |
| 37 | 45 | 74 |
| 62 | 42 | 123 |
| 104 | 42 | 136 |
| 173 | 52 (toxic) | 189 |

NR = Not Run

Mice were inoculated intraperitoneally on day 0 with a million cells of murine leukemia L1210. Drugs were given qd days 1, 3, 5 and 7. Increased life span is presented as a percentage of the mean life span of control mice.

THERAPEUTIC EXAMPLE E

Further elucidation of the dose response of Compound 19 is shown in Table 5. A dose of 288 mg per kg represents the maximum solubility of Compound 19 in water which was utilized as the drug vehicle for this test. As is evident from Table 5, Compound 19 shows an excellent dose response curve when delivered only once on day 1 with significant activity indicated at or about 37 mg per kg.

TABLE 5

RESPONSE OF MICE[1] INOCULATED WITH L1210 CELLS[2] TO TREATMENT WITH COMPOUND 19

| SCHEDULE OF DELIVERY | DOSAGE (mg/kg) | T/C (%) |
|---|---|---|
| qd: day 1 | 288[4] | TOX |
| | 173 | 167 |
| | 104 | 151 |
| | 62 | 135 |
| | 37 | 128 |
| | 22 | 106 |
| | 13 | 106 |
| bid: day 1 | 62 | 184 |
| tid: day 1 | 62 | 183 |
| qid: day 1 | 62 | 194 |

[1]Each treatment group consisted of 3 female BDF$_1$ mice.
[2]Mice were inoculated i.p. with L1210 cells (10[6] per mouse) on day 0.
[3]Drug delivery was by the i.p. route.
[4]Maximum solubility.

THERAPEUTIC EXAMPLE F

In Example F Compound 19 and other known cancer chemotherapeutic agents were bioassayed for activity against neoplastic cells in the brain utilizing the L1210 cell line injected intracranially into test animals. In Table 6-a Compound 19 is compared to a control and in Table 6-b Compound 19 is compared to other known cancer chemotherapeutic agents. As is evident from Table 6-a there is a significant reduction in the number of neoplastic cells in the brain of the test animal after i.p. infection with Compound 19. This is indicative of both activity of Compound 19 and the ability of Compound 19 to cross the blood brain barrier. As is indicative of Table 6-b, Compound 19 shows an excellent therapeutic effect when compared to known chemotherapeutic agents evaluated by this test procedure. Only three known chemotherapeutic agents out of the seven tested showed results approximately equal to or better than those for Compound 19.

TABLE 6-a

BIOASSAY OF L1210-INOCULATED BRAINS $BDF_1$ mice were inoculated intracranially on day 0 with $1 \times 10^5$ L1210 cells. 24 hr later, on day 1, the mice were injected ip with Compound 19 or 0.9% NaCl. 24 hr after drug delivery the brains were collected, homogenized, and injected ip into untreated mice. Each mouse received the equivalent of half a brain. Thereafter, life span was monitored and, using inoculum-response data as a base of comparison, estimates were made of the numbers of viable cells in treated and control brains.

|  | cell/half brain day 2 | | change due to drug | |
| --- | --- | --- | --- | --- |
|  | $\log_{10}$ | cell number | $\log_{10}$ | cells |
| Compound 19 173 mg/kg | 5.42 | 261016 | −1.10 | −92.08% |
| Control | 6.52 | 3295013 | — | — |

TABLE 6-b

VIABLE L1210 CELLS IN MOUSE BRAIN 24-HR AFTER A SINGLE I.P. TREATMENT WITH VARIOUS ANTICANCER DRUGS

| DRUG | DOSAGE (mg/kg) | RESIDUAL CELLS (% of control brain) |
| --- | --- | --- |
| Methotrexate | 12 | 97 |
| Adriamycin | 3 | 89.5 |
| 6-Mercaptopurine | 160 | 37 |
| Cytosine Arabinoside | 1200 | 15 |
| Cyclophosphamide | 140 | 11.5 |
| Compound 19 | 173 | 7.9 |
| Tiazofurin | 1200 | 2.9 |
| BCNU | 20 | 1.6 |

In Examples G through K Compound 19 was tested against L1210 cell lines which had developed resistance to other known cancer chemotherapeutic agents. Depending upon the resistant cell line which was being tested and the mode of administration and/or treatment regimen, Compound 19 showed activity against various cell lines which are resistant to other known chemotherapeutic agents.

THERAPEUTIC EXAMPLE G

In Example G Compound 19 was tested against both L1210 cells and L1210 cells which were resistant to 6-Mercaptopurine, 6-Thioguanine and 6-Thioguanosine. As is evident from the different drug regimens shown, Compound 19 exhibited activity against the drug resistant cells. As was noted above, drugs in the 6-Mercaptopurine family are presently among the drugs of choice for treatment of leukemia. It is thus evident from Table 7-a that Compound 19 is active against cells which have become resistant to these drugs.

TABLE 7-a

L1210 AND L1210/6MP, 6TG CELLS[1] SURVIVING TREATMENT WITH COMPOUND 19

| DRUG DELIVERED[2] (schedule indicated) | DOSAGE (mg/kg/inj) | CELL LINE | |
| --- | --- | --- | --- |
|  |  | L1210 | L1210/6MP, 6TG[3] 6TGR |
| qd: day 1 | 173 | 1.4 | 4.6 |
|  | 104 | 5.4 | 54.5 |
|  | 62 | 0.8 | 15.9 |
| bid: day 1 | 62 | 0.8 | 15.9 |
| tid: day 1 | 62 | 0.4 | 15.9 |

[1]Expressed as % of day zero, intraperitoneal inoculum of $1 \times 10^6$ cells.
[2]Drug delivery was by the intraperitoneal route.
[3]6MP = 6-Mercaptopurine: 6TG = 6-Thioguanine: 6TGR = 6-Thioguanosine.

Table 7-b shows the activity of Compound 19 against cells resistant to the 6-Mercaptopurine family of drugs expressed as increased life span. As is evident from Table 7-b Compound 19 shows efficacy against these resistant cells when the affected animal was treated intraperitoneally.

TABLE 7-b

ACTIVITY OF COMPOUND 19 AGAINST L1210 AND L1210/6MP,6TG WHEN DELIVERED ORALLY OR INTRAPERITONEALLY

| Dosage mg/kg/inj | Drug Schedule | Route | Tumor | | | |
| --- | --- | --- | --- | --- | --- | --- |
|  |  |  | L1210 | | L1210/ 6MP,6TG | |
|  |  |  | % ILS[1] | RCP[2] | ILS | RCP |
| 37 | bid 1,3,5,7 | ip | 79 | (.32) | 66 | (.28) |
|  |  | oral | 49 | (3.73) | 0 |  |
| 62 | bid 1,4,7 | ip | 88 | (.14) | 75 | (.09) |
|  |  | oral | 40 | (8.48) | 0 |  |

[1]% Increase Life Span.
[2]Residual Cell Population.

THERAPEUTIC EXAMPLE H

In Example H, the results of which are shown in Table 8, Cytosine Arabinoside resistant L1210 cells were treated with Compound 19. As is evident from Table 8, Compound 19 showed greater efficacy against this resistant cell line than it did to the parent non-drug resistant L1210 cells. This is indicative of 'collateral activity' of compounds of the invention against resistant cells.

TABLE 8

L1210 AND L1210/ARA-C CELLS[1] SURVIVING TREATMENT WITH COMPOUND 19

| DRUG DELIVERED[2] (qd days indicated) | DOSAGE (mg/kg/inj) | CELL LINE | |
| --- | --- | --- | --- |
|  |  | L1210 | L1210/ARA-C |
| 1 | 173 | 1.4 | 0.02[3] |
| 1, 4, 7 | 173 | 1.1 | 0.6 |
| 1, 4, 7 | 104 | 29.0 | 1.7 |

[1]Expressed as % of day zero, intraperitoneal inoculum of $1 \times 10^6$ cells.
[2]Drug delivery was by the intraperitoneal route.
[3]Indicative of 'collateral activity'.

THERAPEUTIC EXAMPLE I

In Example I Compound 19 was tested against Methotrexate resistant L1210 cells. Depending upon the dose level and the dose regimen, activity can be seen against these Methotrexate resistant cells.

TABLE 9

L1210 AND L1210/MTX CELLS[1] SURVIVING TREATMENT WITH COMPOUND 19

| DRUG DELIVERED[2] | DOSAGE | CELL LINE | |
|---|---|---|---|
| (qd days indicated) | (mg/kg/day) | L1210 | L1210/MTX |
| 1 | 173 | 1.4 | 1.6 |
| 1, 4, 7 | 173 | 1.1 | 33.8 |
| 1, 4, 7 | 104 | 29.0 | 238.4 |

[1]Expressed as % of day zero, intraperitoneal inoculum of $1 \times 10^6$ cells.
[2]Drug delivery was by intraperitoneal route.
[3]MTX = Methotrexate.

THERAPEUTIC EXAMPLE J

In Example J, the results of which are shown in Table 10 below, Compound 19 was tested against 5-Fluorouracil resistant cells. Large dosages of Compound 19 were highly active against these resistant cells.

TABLE 10

L1210 AND L1210/5FU[4] CELLS[1] SURVIVING TREATMENT WITH COMPOUND 19

| DRUG DELIVERED[2] | DOSAGE | CELL LINE | |
|---|---|---|---|
| (qd days indicated) | (mg/kg/day) | L1210 | L1210/FU |
| 1–7 | 104 | 0.04[3] | 3 |
| 1–7 | 62 | 13 | 933 |
| 1, 3, 5, 7 | 173 | 0.2 | 13 |
| 1, 3, 5, 7 | 104 | 17 | 525 |

[1]Expressed as % of day zero, intraperitoneal inoculum of $1 \times 10^6$ cells.
[2]Drug delivery was by intraperitoneal route.
[3]Treatment group included 1 long term survivor which was not included in the calculation of life span.
[4]5FU = 5-Fluorouracil.

Compound 19 has not been found to generate resistant cell lines as per the other known cancer chemotherapeutic agents listed in Tables 7 through 10 above. However, Compound 18 does generate drug resistant cell lines.

THERAPEUTIC EXAMPLE K

In Example K, the results of which are shown in Table 11 below, Compound 19 was tested against drug resistant cell lines developed against Compound 18. As is evident from the results shown in Table 11, Compound 19 differs from Compound 18 only by the state of oxidation between the sulfenamide of Compound 18 and the sulfinamide of Compound 19. As is evident from Table 11 Compound 19 is effective against those L1210 cell lines which have developed resistance against Compound 18. Thus, while Compound 18 may mimic 6-Thioguanosine in that it generates drug resistant cells, the mode of action of Compound 19 is believed to be completely different as is expressed by its activity seen in Example G against 6-Thioguanosine resistant cell lines and its activity in Example K against Compound 18 resistant cell lines.

TABLE 11

L1210 AND L1210/DRUG RESISTANT CELLS[1] SURVIVING TREATMENT WITH COMPOUND 19

| DRUG DELIVERED[2] | DOSAGE | CELL LINE | |
|---|---|---|---|
| (qd days indicated) | (mg/kg/day) | L1210 | L1210/ COMPOUND 18 |
| qd: day 1 | 173 | 1.4 | 7.5 |
| | 104 | 5.4 | 17.9 |
| | 62 | 8.5 | 100.0 |
| bid: day 1 | 62 | 0.8 | 27.4 |

[1]Expressed as % of day zero, intraperitoneal inoculum of $1 \times 10^6$ cells.
[2]Drug delivery was by intraperitoneal route.

THERAPEUTIC EXAMPLE L

In this Example Compounds 18 and 19 were tested singularly and then in combination first given both together and then given in different orders. As is evident from the result tabulated in Table 12 both Compounds 18 and 19 induced increases in life span in the test animals with the activity of the compounds given simultaneously or sequentially being similar or even inferior to that seen for Compound 19 by itself.

TABLE 12

COMBINED DRUG TREATMENT OF L1210: COMPOUND 19 AND COMPOUND 18

| Schedule of Delivery[1] | | |
|---|---|---|
| Day 1 | Day 2 | % ILS[2] |
| Compound 19 | | 88 |
| Compound 18 | | 51 |
| Compound 19 and Compound 18 | | 58 |
| Compound 19 | Compound 18 | 91 |
| Compound 18 | Compound 19 | 84 |

[1]Dosages: Compound 19 173 mg/kg
Compound 18 22 mg/kg.
[2]% Increase Life Span.

THERAPEUTIC EXAMPLE M

In Example M a further example was run similar to that of Exhibit L except that Compound 19 was utilized in conjunction with the known chemotherapeutic agent Tiazofurin. As is evident from the results tabulated in Table 13 increased activity is seen when Compound 19 and Tiazofurin are given sequentially. Sequence dependency was also observed with the best result being produced when Compound 19 preceded Tiazofurin.

TABLE 13

COMBINED DRUG TREATMENT OF L1210: COMPOUND 19 AND TIAZOFURIN

| Schedule of Delivery[1] | | |
|---|---|---|
| Day 1 | Day 2 | % ILS[2] |
| Compound 19 | | 81 |
| Tiazofurin | | 44 |
| Compound 19 and Tiazofurin | | 69 |
| Tiazofurin | Compound 19 | 100 |
| Compound 19 | Tiazofurin | 150 |

[1]Dosages: Compound 19 173 mg/kg Tiazofurin 22 mg/kg
[2]Increase Life Span

THERAPEUTIC EXAMPLE N

In Example N other compounds of the invention were tested against L1210 cells. All of the compounds listed in Table 14 exhibit activity. Further, Table 14 shows the maximum solubility (in water unless otherwise indicated) and the maximum tolerated dose. Activity in Table 14-a is tabulated as both increases in life span and as cells surviving treatment and that in table 14-b as T/C.

TABLE 14-a

RESPONSE OF L1210 INOCULATED BDF$_1$ MICE TO COMPOUNDS OF THE INVENTION

| COMPOUND # | MAX. SOL. DOSAGE[2] (MG/KG) | MAX. TOLERATED DOSAGE (MG/KG) | % ILS | CELLS SURVIVING TREATMENT (% OF DAY 0 INNOC.) |
|---|---|---|---|---|
| 20 | 62 | 62 | 28 | 40 |
| 38 | 173 | 173 | 29 | 27 |
| 15 | 800 | 104 | 33 | 16 |
| 24 | 480 | 288 | 34 | 17 |
| 12 | 173 | 173 | 39 | 13 |
| 8 | 480 | 173 | 43 | 6.4 |
| 22 | 173 | 173 | 47 | 6.0 |
| 29 | 480 | 480 | 59 | 1.7 |
| 23 | 480 | 173 | 59 | 2.0 |
| 30 | 288 | 288 | 59 | 1.7 |
| 2 | 104(NaOH) | 104 | 63 | 2.0 |
| 2 | 62(DMSO) | 37 | 66 | 0.8 |
| 14 | 800 | 288 | 66 | 1.0 |
| 6 | 480 | 480 | 67 | 2.8 |
| 16 | 800 | 173 | 69 | 1.0 |
| 18 | 22 | 22 | 85 | 0.3 |

[1] Above data resulted from single QD day 1 treatment of BDF$_1$ mice on day 0 with $10^6$ cell L1210. Both cell inoculation and treatment were IP.
[2] In water unless otherwise indicated.

TABLE 14-b

RESPONSE OF L1210 INOCULATED BDF$_1$ MICE TO COMPOUNDS OF THE INVENTION

| COMPOUND # | MAX. SOL. DOSAGE[2] (MG/KG) | T/C |
|---|---|---|
| 42 | 104(NaOH) | 172 |
| 43 | 480 | 130 |
| 45 | 480 | 172 |
| 50 | 800 | 140 |
| 55 | 288 | 125 |

[1] Above data resulted from single QD day 1 treatment of BDF$_1$ mice on day 0 with $10^6$ cell L1210. Both cell inoculation and treatment were IP.
[2] In water unless otherwise indicated.

Compound 19 was also tested against a variety of solid tumors. No activity was noted against B-16 melanoma, Lewis lung carcinoma or human lung carcinoma LX-1. Activity, however, was noted in a variety of other solid tumors as per examples O through S below.

THERAPEUTIC EXAMPLE O

In this example Compound 19 was tested against reticulum cell sarcoma M5076. For this and certain other tests below, test results are shown as $\delta T/\delta C$. Utilizing this protocol the difference in tumor weight before treatment and after treatment of the treated animals compared to the control animals is determined. As is seen in Table 15, Compound 19 exhibited activity against this cell line and shows a dose response for this activity.

TABLE 15

RESPONSE OF RETICULUM CELL SARCOMA M5076[1] TO TREATMENT WITH COMPOUND 19

| SCHEDULE OF DELIVERY[2] (qd days indicated) | DOSAGE (mg/kg/inj) | TUMOR WT[3] staging[4] day | (Mean ± 1SD) evaluation[5] day | $\delta T/\delta C$ |
|---|---|---|---|---|
| 1,3,5,7,9,11 | 173.0 | 354 ± 81 | 409 ± 385 | 5.0 |
|  | 138.4 | 355 ± 79 | 855 ± 325 | 45.4 |
|  | 110.8 | 396 ± 116 | 1121 ± 343 | 65.8 |
|  | 0 | 396 ± 104 | 1498 ± 498 | — |

[1] C57B1/6 female mice (7/group) were inoculated s.c. with $1 \times 10^6$ M5076 cells on day 0.
[2] Drug was delivered by the i.p. route.
[3] Tumor weight was estimated from caliper measurements using the formula: tumor wt. (mg) = $w^2 l/4.45$.
[4] Treatment was initiated on staging day (day 15 post inoculation).
[5] Day 12 post initiation of treatment.

THERAPEUTIC EXAMPLE P

In Example P Compound 19 was tested against human mammary carcinoma MX-1. As per the results tabulated in Table 16, Compound 19 exhibited a dose response against this solid tumor.

TABLE 16

RESPONSE OF HUMAN MAMMARY CARCINOMA MX-1[1] TO TREATMENT WITH COMPOUND 19

| SCHEDULE OF DELIVERY[2] (qd days indicated) | DOSAGE (mg/kg/inj) | TUMOR WT[3] staging[5] day | (Mean ± 1SD) evaluation[6] day | $\delta T/\delta C$[4] |
|---|---|---|---|---|
| 1,3,5,7,9,11 | 173.0 | 323 ± 127 | 489 ± 104 | 17.6 |
|  | 138.4 | 330 ± 118 | 884 ± 415 | 58.9 |
|  | 110.8 | 321 ± 132 | 943 ± 297 | 66.1 |

TABLE 16-continued
RESPONSE OF HUMAN MAMMARY CARCINOMA MX-1[1]
TO TREATMENT WITH COMPOUND 19

| SCHEDULE OF DELIVERY[2] (qd days indicated) | DOSAGE (mg/kg/inj) | TUMOR WT[3] staging[5] day | (Mean ± 1SD) evaluation[6] day | δT/δC[4] |
|---|---|---|---|---|
| | 0 | 325 ± 112 | 1266 ± 695 | — |

[1]CD-1 nu/nu female mice (7 per group) were implanted s.c. with fragments (<25 mg ea.) of MX-1 carcinoma on day 0.
[2]Drug delivery was by the i.p. route.
[3]Tumor weight was estimated from caliper measurements using the formula: tumor wt (mg) = $w^2 1/4.45$.
[4]NCI guidelines suggest a δT/δC ≦ 20% for demonstration of moderate activity.
[5]Treatment was initiated on staging day (day 17 post implant).
[6]Day 15 post initiation of treatment.

THERAPEUTIC EXAMPLE Q

In Example Q Compound 19 was tested against Colon 26 Adenocarcinoma. Except when given once a day in the regimen on days 1, 4 and 7, for the other dosages and test regimens compound 19 exhibited activity against this tumor.

TABLE 17
RESPONSE OF MICE[1] BEARING COLON 26 ADENO-CARCINOMA[2] TO TREATMENT WITH COMPOUND 19

| SCHEDULE OF DELIVERY[3] | DOSAGE (mg/kg/inj) | MEDIAN SURVIVAL TIME (days post inoculation) | T/C[4] (%) |
|---|---|---|---|
| qd: days 1, 4, 7 | 173 | 31 | 135 |
| | 104 | 31 | 135 |
| qd: days 1, 3, 5, 7 | 173 | 42 | 183 |
| | 104 | 34 | 148 |
| qd: days 1-7 | 104 | 38 | 165 |
| | 62 | 40 | 174 |
| bid: days 1, 4, 7 | 104 | 17[5] | — |
| bid: days 1, 4, 7 | 62 | 45 | 196 |

[1]Each treatment group consisted of 11 female CDF$_1$ mice.
[2]3 × 10$^6$ cells of Colon 26 Adenocarcinoma were implanted i.p. on day 0.
[3]Drug delivery was by the i.p. route.
[4]NCI guidelines suggest a T/C ≧ 150% for demonstration of significant activity.
[5]Treatment group included 6 toxic deaths.

THERAPEUTIC EXAMPLE R

Compound 19 was further tested against Human Colon Adenocarcinoma CX-1. For comparison purposes the activity of other clinically active antitumor agents is shown in Table 18-a. Activity against this tumor system is indicated at a δT/δC value of less than 20.

TABLE 18-a
ACTIVITY OF CLINICALLY ACTIVE ANTITUMOR AGENTS AGAINST CX-1[1]

| NSC # | DRUG | ACTIVITY RATING δT/δC[2] |
|---|---|---|
| 740 | Methotrexate | 66 |
| 752 | 6-Thioguanine | 81 |
| 755 | 6-Mercaptopurine | 99 |
| 3053 | Actinomycin D | 73 |
| 3088 | Chlorambucil | 60 |
| 8806 | Melphalan | 101 |
| 13875 | Hexamethylmelamine | 85 |
| 19893 | 5-Fluorouracil | 88 |
| 26271 | Cyclophosphamide | 113 |
| 26980 | Mitomycin C | 62 |
| 45388 | DTIC | 92 |
| 49842 | Vinblastine | 119 |
| 63878 | Cytosine arabinoside | 73 |
| 67574 | Vincristine | 89 |
| 77213 | Procarbazine | 60 |
| 79037 | CCNU | 77 |
| 95441 | Methyl CCNU | 83 |
| 119875 | Cis-Platinum | 66 |
| 123127 | Adriamycin | 72 |
| 125066 | Bleomycin | 51 |
| 178248 | Chlorozotocin | 75 |
| 409962 | BCNU | 63 |

[1]Data taken from: A. Goldin, et al, Current Results Of The Screening Program Of The Division Of Cancer Treatment, National Cancer Institute, Europ. J. Cancer, Vol. 17, 129–142, (1981).
[2]Activity indicated at δT/δC ≦20.

In a like manner Compound 19 was tested against this tumor system with the results shown in Table 18-b. As is shown, at the 173 mg level when drug was given on days 1, 4, 7, 10 and 13, activity against this tumor system is demonstrated.

TABLE 18-b
RESPONSE OF HUMAN COLON ADENOCARCINOMA CS-1[1]
TO TREATMENT WITH COMPOUND 19

| SCHEDULE OF DELIVERY[2] (qd days indicated) | DOSAGE (mg/kg/inj) | TUMOR WT[3] staging[5] day | (mean ± 1SD) evaluation[6] day | δT/δC[4] |
|---|---|---|---|---|
| 1, 3, 5, 7, 9 | 173.0 | 229 ± 141 | 364 ± 254 (16) | 39.9 |
| 1, 4, 7, 10, 13 | 173.0 | 226 ± 125 | 279 ± 121 (17) | 15.8 |
| 1, 3, 5, 7 | 173.0 | 222 ± 79 | 302 ± 144 (12) | 38.5 |
| 1, 4, 7, 10 | 173.0 | 226 ± 103 | 402 ± 187 (16) | 52.1 |
| 1, 3, 5, 7, 9, 11 | 138.4 | 220 ± 80 | 358 ± 125 (15) | 46.6 |
| 1, 4, 7, 10, 13, 16 | 138.4 | 215 ± 81 | 296 ± 186 (12) | 38.9 |
| 1, 3, 5, 7, 9 | 138.4 | 226 ± 120 | 278 ± 114 (12) | 25.0 |
| 1, 4, 7, 10, 13 | 138.4 | 225 ± 104 | 375 ± 155 (15) | 50.7 |
| | 0 | 218 ± 81 | 426 ± 195 (12) | — |
| | 0 | 218 ± 81 | 514 ± 252 (15) | — |
| | 0 | 218 ± 81 | 556 ± 238 (16) | — |

TABLE 18-b-continued
RESPONSE OF HUMAN COLON ADENOCARCINOMA CS-1[1] TO TREATMENT WITH COMPOUND 19

| SCHEDULE OF DELIVERY[2] (qd days indicated) | DOSAGE (mg/kg/inj) | TUMOR WT[3] staging[5] day | (mean ± 1SD) evaluation[6] day | δT/δC[4] |
|---|---|---|---|---|
| | 0 | 218 ± 81 | 553 ± 231 (17) | — |

[1]CD-1 nu/nu female mice (6 per group) were implanted s.c. with fragments (<25 mg ea.) of CX-1 adenocarcinoma on day 0.
[2]Drug delivery was by the i.p. route.
[3]Tumor weight was estimated from caliper measurements using the formula: tumor wt (mg) = $w^2$ 1/4.45.
[4]NCI guidelines suggest a T/C ≦20% for demonstration of moderate activity.
[5]Treatment was initiated on staging day (day 33 post implant).
[6]The day of occurrence (shown in parenthesis) of optimum δ/δ % between day 12 and day 21 post initiation of treatment.

It is indicative that activity against this tumor system is possible utilizing optimum dose scheduling of Compound 19 against this tumor system.

THERAPEUTIC EXAMPLE S

Compound 19 was also tested against Murine Glioma 261. In this test activity is indicated at levels of T/C below 42%. As is shown in Table 19, Compound 19 is active at various doses against this tumor system.

TABLE 19
RESPONSE OF MURINE GLIOMA 261[1] TO TREATMENT WITH COMPOUND 19 ATTAINED

| SCHEDULE OF DELIVER[2] | DOSAGE (mg/kg/inj) | TUMOR WT[3] (mg) | T/C[5] (%) |
|---|---|---|---|
| qd: days 1–9 | 104 | 5 ± 5[4] | 1.4 |
| | 62 | 137 ± 124 | 39.3 |
| | 37 | 119 ± 105 | 34.1 |
| | 22 | 80 ± 130 | 22.9 |
| | 0 | 349 ± 139 | — |

[1]C57B1/6 male mice (6/group) were implanted s.c. with fragments (<25 mg/ea) of Glioma 261 on day 0.
[2]Drug was delivered by the i.p. route.
[3]On day 10 post implant, tumor sizes were estimated from caliper measurements using the formula: tumor wt(mg) = $w^2$ 1/4.45.
[4]Mean ± 1SD.
[5]Activity indicated at or below T/C of 42%.

THERAPEUTIC EXAMPLE T

As an example of activity among the different members of the oxidation series represented by sulfenamides, sulfinamides and sulfonamides comparison of activity of Compounds 18, 19, and 20 is shown in Table 19-a and is summarized in Table 19-b. As is evident from the summaries in Table 19-b, Compounds 18 and 19 effectively cross the blood brain barrier and thus are active intracranially whereas at the high oxidation state of Compound 20 no intracranial activity is seen. Oral activity is seen for both Compounds 18 and 19 but not present in Compound 20. Contrasted to this is activity against resistant cells wherein Compounds 19 and 20 are active but Compound 18 in fact shows no activity. As was shown in Example K, Table 11 above, Compound 19 in fact was active against cells which developed resistance to Compound 18.

TABLE 19-a

| Activity against I. C. L1210 cells | | Activity against I.P L1210 cells with oral drug administration | | | Activity against I.P. L1210 cells resistant to 6MP, 6TG, 6TGR | | |
|---|---|---|---|---|---|---|---|
| I.P. Dosage (mg/kg) | Cell Kill (x) | Schedule | Dosage (mg/kg) | T/C (%) | Schedule | Dosage (mg/kg) | T/C (%) |
| | | | Compound 18 | | | | |
| 22 | 57.3 | qd:dl | 22 | 153.0 | qd:dl | 22 | 93.8 |
| | | | 13 | 147.0 | | | |
| | | | 8 | 147.0 | | | |
| | | | Compound 19 | | | | |
| 173 | 92.1 | qd:d1, 4, 7 | 173 | 138.5 | qd:dl | 173 | 144.5 |
| | | | 104 | 138.5 | | 104 | 122.2 |
| | | | 62 | 144.6 | | 62 | 127.3 |
| | | | 37 | 144.6 | bid:dl | 104 | 150.0 |
| | | bid:d1, 3, 5, 7 | 37 | 148.6 | | 62 | 133.3 |
| | | bid:d1, 4, 7 | 62 | 140.0 | tid:dl | 62 | 133.3 |
| | | | | | bid:d1, 3, 5, 7 | 37 | 165.6 |
| | | | | | bid:1, 4, 7 | 62 | 175.0 |
| | | | Compound 20 | | | | |
| 62 | 0.0 | bid:d1, 4, 7 | 62 | 103.3 | bid:d1, 4, 7 | 62 | 163.3 |
| | | | 37 | 103.3 | | 37 | 130.0 |
| | | | 22 | 103.3 | | 22 | 106.7 |

The different compounds of the sulfinamide, sulfenamide and sulfonamide series as is demonstrated by Compound 18, 19 and 20 show various advantages and disadvantages with the sulfinamide Compound 19 having optimization of certain properties. Compound 19 shares the best properties of both Compounds 18 and 20.

TABLE 19-b

| | ACTIVITY VS. I.C. CELLS | ORAL ACTIVITY | ACTIVITY VS. L1210/ 6MP:6TG:6TGR |
|---|---|---|---|
| Compound 18 | + | + | — |
| Compound 19 | + | + | + |
| Compound 20 | — | — | + |

Compound 19 exists as two enantiomers. The above test results for Compound 19 were done on the racemic mixture of these enantiomers. Further, separation of these enantiomers to a high degree of (but not absolute) purity has been effected. The separate enantiomers have been independently tested and further tested as contrived mixtures of known amounts of the enantiomers. Of the two purified enantiomers, enantiomer B shows a higher solubility than enantiomer A and the racemic mixture exhibits solubility characteristics of enantiomer B exhibiting solubility at about 17.3 mg per ml. In contrast to this enantiomer A exhibits solubility of about 3.7 mg per ml. The two enantiomers present comparable activity, however, because of the solubility of enantiomer A is less than enantiomer B, tests with enantiomer A have been done at a much lower dosage level.

THERAPEUTIC EXAMPLE U

In this example the enantiomers of Compound 19 labeled enantiomer A and enantiomer B were tested independent of one another. The results of these tests are indicated utilizing two different protocols as are shown in Tables 20-a and 20-b. Enantiomer A shows greater activity with respect to enantiomer B because of solubility differences.

TABLE 20-a

LIFE SPAN (% T/C) OF L1210 INOCULATED[1] MICE TREATED[2] WITH COMPOUND 19 ENANTIOMER A OR ENANTIOMER B

| DRUG | DOSAGE (mg/kg) | T/C (%) |
|---|---|---|
| Compound 19 | | |
| Enantiomer A | 37 | 108.7 |
| Enantiomer B | 173 | 144.9 |

[1]BDF$_1$ female mice were inoculated i.p. on day 0 with 10$^6$ L1210 cells.
[2]Drug was administered i.p. dq:day 1.

TABLE 20-b

L1210 CELLS[1] SURVIVING TREATMENT[2] WITH COMPOUND 19 ENANTIOMER A OR ENANTIOMER B

| DRUG | DOSAGE (mg/kg) | % OF ORIGINAL INOCULUM |
|---|---|---|
| Compound 19 | | |
| Enantiomer A | 37 | 182.8 |
| Enantiomer B | 173 | 7.5 |

[1]BDF$_1$ female mice were inoculated i.p. on day 0 with 10$^6$ L1210 cells.
[2]Drug was administered i.p. dq:day 1.

THERAPEUTIC EXAMPLE V

In this example different regimens of dosages for enantiomer A of Compound 19 were utilized and the results were tabulated in Table 21. The percent of contamination of enantiomer A with enantiomer B and with a further contaminate comprising Guanosine and Compound 20 was tested using HPLC. As is evident from Table 21, when the dosage of enantiomer A was divided into multiple dose regimens effective therapy was indicated.

TABLE 21

EFFECT OF COMPOUND 19 ENANTIOMER-A ON THE MEANS LIFE SPAN OF BDF$_1$ MICE INOCULATED I.P. WITH 1 × 10$^6$ CELLS OF L1210

| Drug Delivered (mg/kg/inj) | Schedule of Delivery | Total Drug (mg/kg) Delivered as | | | % ILS | Cells Surviving Treatment (% of original inoc. |
|---|---|---|---|---|---|---|
| | | A | B | Contaminant | | |
| 37 | qd, day 1 | 35.47 | 0.63 | 0.90 | 22 | 64 |
| 37 | bid, day 1 | 70.94 | 1.26 | 1.80 | 44 | 10 |
| 37 | tid, day 1 | 106.41 | 1.89 | 2.70 | 72 | 1 |
| 37 | qid, day 1 | 141.88 | 2.52 | 3.60 | 72 | 1 |
| 37 | qid, day 1 | 177.35 | 3.15 | 4.50 | 0 | tox |

As shown, all injections were made on day 1. For mice treated more than once, treatment was completed within 20 minutes. Enantiomer A was 95.87% A and 1.71% B: thus, these two enantiomers comprised 97.58% of the material delivered. The A:B ratio was 95.87:1.71. There were 3 mice in each treatment group.

THERAPEUTIC EXAMPLE W

In this example, concocted mixtures of enantiomers A and B were made. In addition, these mixtures were contaminated with small amount of contaminants comprising Guanosine and Compound 20. As is indicative from the results shown in Table 22, activity does not reside with only one or the other of the two enantiomers but is apparently optimized in mixtures of the enantiomers. It is presently believed a 50/50 mixture of the enantiomers of compound 19 is suggested for use in antitumor compositions of this compound.

TABLE 22

EFFECTS OF VARIOUS RATIOS OF COMPOUND 19-ENANTIOMERS A AND B ON THE MEAN LIFE SPAN OF BDF$_1$ MICE INOCULATED I.P. WITH 1 × 10$^6$ CELLS OF L1210

| Drug Delivered (mg/kg/inj) | A/B Ratio | Total Drug (mg/kg) Delivered as | | | % ILS | Cells Surviving Treatment (% of original inoc. |
|---|---|---|---|---|---|---|
| | | A | B | Contaminant | | |
| 62 | 90/10 | 55.58 | 6.42 | 1.74 | 14 | 100 |
| 104 | 70/30 | 73.53 | 31.13 | 3.50 | 20 | 58 |
| 173 | 50/50 | 87.17 | 85.83 | 5.09 | 57 (2 tox) | 2 |
| 173 | 30/70 | 59.03 | 113.97 | 6.31 | 31 | 19 |
| 173 | 10/90 | 19.08 | 153.92 | 4.14 | 37 | 11 |
| 173 | 90/10 | 156.91 | 16.09 | 4.88 | 62 (2 tox) | 1 |
| 173 | 70/30 | 121.26 | 51.74 | 5.83 | 43 (4 tox) | 7 |

TABLE 22-continued
EFFECTS OF VARIOUS RATIOS OF COMPOUND 19-ENANTIOMERS
A AND B ON THE MEAN LIFE SPAN OF BDF$_1$ MICE INOCULATED I.P.
WITH $1 \times 10^6$ CELLS OF L1210

| Drug Delivered (mg/kg/inj) | A/B Ratio | Total Drug (mg/kg) Delivered as | | | % ILS | Cells Surviving Treatment (% of original inoc. |
|---|---|---|---|---|---|---|
| | | A | B | Contaminant | | |
| 173 | 50/50 | 87.69 | 85.48 | 5.10 | 62 (2 tox) | 1 |
| 173 | 30/70 | 54.74 | 118.26 | 3.29 | 40 | 8 |
| 173 | 10/90 | 19.36 | 153.64 | 3.44 | 29 | 25 |

All treatments were made qd, day 1. Each treatment group consisted of 5 mice: the postinoculation life span of these treated mice was compared with that of 9 control mice that were injected with a 0.9% solution of NaCl.

For delivery to a host inflicted with a neoplastic disease compounds of the invention can be formulated in various formulations to prepare pharmaceutical compositions containing the compounds of the invention as active ingredients. The following illustrative examples are given for the formulations of such pharmaceutical compositions utilizing Compound 19 as the illustrative compound. In these examples, Pharmaceutical Preparative Example 1 illustrates the use of the compounds of the invention in injectables suitable for intravenous or other types of injection into the host animal. Pharmaceutical Preparative Example 2 is directed to an oral syrup preparation, Pharmaceutical Preparative Examples 3 to an oral capsule preparation and Pharmaceutical Preparative Example 4 to oral tablets. Pharmaceutical Preparative Example 5 is directed to use of the compounds of the invention in suitable suppositories. For Pharmaceutical Preparative Examples 1 through 5, the ingredients are listed followed by the methods of preparing the composition.

PHARMACEUTICAL PREPARATIVE EXAMPLE 1

INJECTABLES

| | |
|---|---|
| Compound 19 | 250 mg-1000 mg |
| Water for Injection USP q.s. | |

Compound 19 is dissolved in the water and passed through a 0.22; filter. The filtered solution is added to ampoules or vials, sealed and sterilized.

PHARMACEUTICAL PREPARATIVE EXAMPLE 2

SYRUP 250 mg Active ingredient/5 ml syrup

| | |
|---|---|
| Compound 19 | 50.0 g |
| Purified Water USP q.s. or | 200 ml |
| Cherry Syrup q.s. ad | 1000 ml |

Compound 19 is dissolved i the water and to this solution the syrup is added with mild stirring.

PHARMACEUTICAL PREPARATIVE EXAMPLE 3

CAPSULES 100 mg 250 mg or 500 mg

| | |
|---|---|
| Compound 19 | 500 g |
| Lactose WSP, Anhydrous q.s. or | 200 g |
| Sterotex Powder HM | 5 g |

Combine compound 19 and the Lactose in a twin-shell blender equipped with an intensifier bar. Tumble blend for two minutes, followed by blending for one minute with the intensifier bar and then tumble blend again for one minute. A portion of the blend is then mixed with the Sterotex Powder, passed through a #30 screen and added back to the remainder of the blend. The mixed ingredients are then blended for one minute, blended for the intensifier bar for thirty seconds and tumble blended for an additional minute. Appropriate sized capsules are filled with 141 mg, 352.5 mg or 705 mg of the blend, respectively, for the 100 mg, 260 mg and 500 mg containing capsules.

PHARMACEUTICAL PREPARATIVE EXAMPLE 4

TABLETS 100 mg, 200mg or 500 mg

| | |
|---|---|
| Compound 19 | 500 g |
| Corn Starch NF | 200.0 g |
| Cellulose Microcrystalline | 46.0 g |
| Sterotex Powder HM | 4.0 g |
| Purified Water q.s. or | 300.0 ml |

Combine the corn starch, the cellulose and Compound 19 together in a planetary mixer and mix for two minutes. Add the water to this combination and mix for one minute. The resulting mix is spread on trays and dried in a hot air oven at 50° C. until a moisture level of to 2 percent is obtained. The dried mix is then milled with a Fitzmill through a #RH2B screen at medium speed. The Sterotex Powder is added to a portion of the mix and passed through a #30 screen and added back to the milled mixture and the total blended for five minutes by drum rolling. Compressed tables of 150 mg, 375 mg and 750 mg respectively, of the total mix are formed with appropriate sized punches for the 100 mg, 250 mg or 500 mg containing tables.

PHARMACEUTICAL PREPARATIVE EXAMPLE 5

SUPPOSITORIES 250 mg, 500 mg or 1000 mg per 3 g

| | 250 mg | 500 mg | 1000 mg |
|---|---|---|---|
| Compound 19 | 250 mg | 500 mg | 1000 mg |
| Polyethylene Glycol 1540 | 1925 mg | 1750 mg | 1400 mg |
| Polyethylene Glycol 8000 | 825 mg | 750 mg | 600 mg |

Melt the Polyethylene Glycol 1540 and the Polyethylene Glycol 8000 together at 60° C. and dissolve Compound 19 into the melt. Mold this total at 25° C. into appropriate suppositories.

We claim:

1. A compound of the structure:

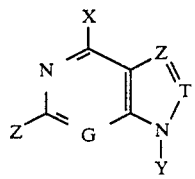

wherein
Z is H or —NH$_2$;
X is —S—NH$_2$,

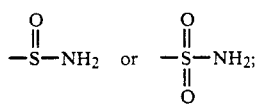

T is C—H, G is N and O is N; or
T is C—H, G is N and O is C—H; or
T is N, G is N and O is C—H; or
T is C—H, G is C—H and O is N;
Y is H or an α-pentofuranose or β-pentofuranose of the formula:

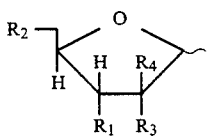

wherein R$_1$ and R$_2$ independently are H, OH, —O-acyl or

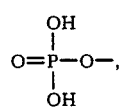

or together R$_1$ and R$_2$ are

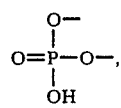

and R$_3$ and R$_4$ are H or one of R$_3$ or R$_4$ is OH and the other is H; provided that when Y is H, Z is —NH$_2$; and
pharmaceutically acceptable salts thereof.

2. A compound of claim 1 wherein:
Z is —NH$_2$.

3. A compound of claim 1 wherein:
T is C—H; and
G and Q are N.

4. A compound of claim 1 wherein:

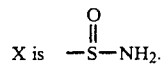

5. A compound of claim 1 wherein:
Y is a β-pentofuranose of the formula:

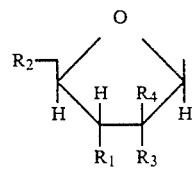

6. A compound of claim 5 wherein:
R$_3$ is OH and R$_4$ is H.

7. A compound of claim 5 wherein:

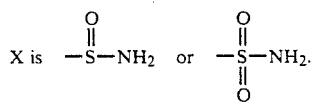

8. A compound of claim 5 wherein:
R$_1$ and R$_2$ are OH.

9. A compound of claim 5 wherein:
Z is —N$_2$.

10. A compound of claim 7 wherein:

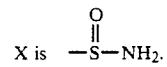

11. A compound of claim 6 wherein:
wherein R$_1$ and R$_2$ independently are OH or

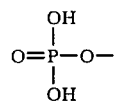

or together R$_1$ and R$_2$ are

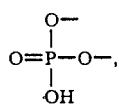

and pharmaceutically acceptable salts thereof.

12. 2-Amino-9-β-D-ribofuranosyl-9H-purine-6-sulfenamide.

13. 2-Amino-9-β-D-ribofuranosyl-9H-purine-6-sulfinamide.

14. 2-Amino-9-β-D-ribofuranosyl-9H-purine-6-sulfonamide.

15. 2-Amino-9-(2-deoxy-β-D-erythro-pentofuranosyl)-9H-purine-6-sulfinamide.

16. 2-Amino-9-β-D-ribofuranosyl-9H-purine-6-sulfinamide 3′,5′-cyclic phosphate.

17. 2-Amino-9-β-D-ribofuranosyl-9H-purine-6-sulfinamide 5'-monophosphate.

18. An pharmaceutical composition containing as its active ingredient an effective amount of a compound selected from compounds of the structure:

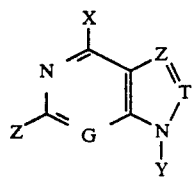

wherein
Z is H or —NH$_2$;
X is —S—NH$_2$,

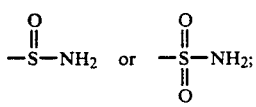

T is C—H, G is N and O is N; or
T is C—H, G is N and O is C—H; or
T is N, G is N and O is C—H; or
T is C—H, G is C—H and O is N;
Y is H or an α-pentofuranose or β-pentofuranose of the formula:

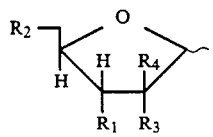

wherein R$_1$ and R$_2$ independently are H, OH, —O-acyl or

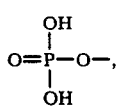

or together R$_1$ and R$_2$ are

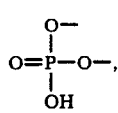

and R$_3$ and R$_4$ are H or one of R$_3$ or R$_4$ is OH and the other is H; provided that when Y is H, Z is —NH$_2$; and pharmaceutically acceptable salts thereof; in an inert carrier thereof.

19. A composition of claim 18 wherein:
Z is —NH$_2$;
T is C—H; and
G and Z are N; and
Y is a β-pentofuranose of the formula:

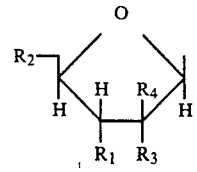

20. A composition of claim 19 wherein:
R$_3$ and R$_4$ are H or R$_3$ is OH and R$_4$ is H.
21. A composition of claim 19 wherein:

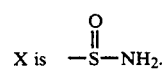

22. An pharmaceutical composition containing as its active ingredient an effective amount of a compound selected from the group consisting of:
2-Amino-9-β-D-ribofuranosyl-9H-purine-6-sulfenamide,
2-Amino-9-β-D-ribofuranosyl-9H-purine-6-sulfinamide,
2-Amino-9-β-D-ribofuranosyl-9H-purine-6-sulfonamide,
2-Amino-9-(2-deoxy-β-D-erythro-pentofuranosyl)-9H-purine-6-sulfinamide,
2-Amino-9-β-D-ribofuranosyl-9H-purine-6-sulfinamide 3',5'-cyclic phosphate, and
2-Amino-9-β-D-ribofuranosyl-9H-purine-6-sulfinamide 5'-monophosphate; in an inert carrier thereof.

23. A composition of claim 22 wherein said compound is:
2-Amino-9-β-D-ribofuranosyl-9H-purine-6-sulfinamide.

24. A process for preparing a compound of the structure

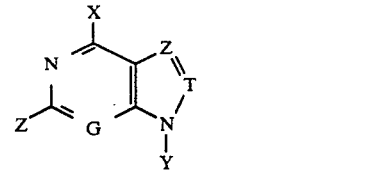

wherein
Z is H or —NH$_2$;
X is —S—NH$_2$,

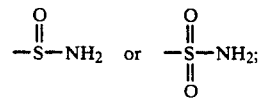

T is C—H, G is N and W is N; or
T is C—H, G is N and O is C—H; or
T is N, G is N and O is C—H; or
T is C—H, G is C—H and O is N;
Y is H or an α-pentofuranose or β-pentofuranose of the formula:

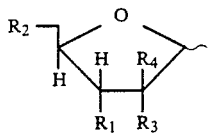

wherein R₁ and R₂ independently are H, OH, —O-acyl or

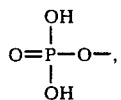

or together R₁ and R₂ are

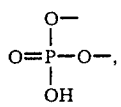

and R₃ and R₄ are H or one of R₃ or R₄ is OH and the other is H; provided that when Y is H, Z is —NH₂; comprising the steps of:

treating a compound of said structure wherein X is =S with chloramine to form a compound of said structure wherein X is —S—NH₂;

isolating said compound.

25. The process of claim 24 further including:
treating a compound of said structure wherein X=—S—NH₂ with an oxidizing agent to form a compound of said structure wherein

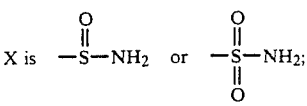

isolating said compound.

26. The process of claim 24 further including:
treating said compound of said structure wherein X is —S—NH₂ with one equivalent of said oxidizing agent to form a compound of said structure wherein

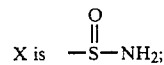

isolating said compound.

27. The process of claim 24 further including:
treating said compound of said structure wherein X is —S—NH₂ with an excess of said oxidizing agent to form a compound of said structure wherein

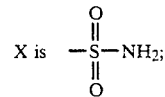

isolating said compound.

28. The process of claim 25 including:
selecting m-chloroperoxybenzoic acid as said oxidizing agent.

* * * * *

UNITED STATES PATENT AND TRADEMARK OFFICE
CERTIFICATE OF CORRECTION

PATENT NO. : 5,026,836   Page 1 of 12
DATED : June 25, 1991
INVENTOR(S) : Roland K. Robins, et al It is certified that error appears in the above-indentified patent and that said Letters Patent is hereby corrected as shown below:

On the title page, In Item [56], "Publications" right hand side: line 14 after "2-Amino-9-" insert --β--. Line 18, "Leudemia" should read --Leukemia--. Line 21, after "2-Amino-9-" insert --β--.

Abstract: line 2, after "3", insert -- - --.
          line 2, after "7", insert -- - --.
          line 3, after "8", insert -- - --.
the unlabelled figure on lines 31-39, that portion of the figure reading:

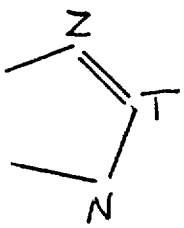

should read as:

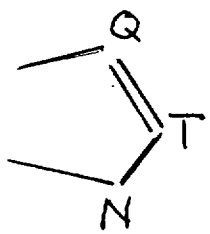

UNITED STATES PATENT AND TRADEMARK OFFICE
CERTIFICATE OF CORRECTION

PATENT NO. : 5,026,836
DATED : June 25, 1991
INVENTOR(S) : Roland K. Robins, et al It is certified that error appears in the above-indentified patent and that said Letters Patent is hereby corrected as shown below:

Column 1, line 10, after "1987," insert a space.

Column 1, line 56, "line" should be --lines--.

Column 1, line 62, after "Thus" insert --,--.

Column 2, line 26, after "3" insert -- - --

Column 2, line 26, between "7" and "deaza" insert -- - --.

Column 2, line 27, between "8" and "aza" insert -- - --.

Column 4, line 10, after "Further" insert --,--.

Column 4, line 57, "2-deoxy-β-D-erythropentofuranosyl" should read --2-deoxy-β-D-erythro-pentofuranosyl--.

Column 6, line 11-12, "6mercaptopurine" should read --6-mercaptopurine--.

Column 6, line 18, after "Generally" insert --,--.

Column 9, line 39, "1.89" should read --31.89--.

Column 10, line 49, after "(0.299g," insert --1.0--.

Column 10, line 62, "SOO" should read --S=O--.

Column 11, line 39, after "285 nm" insert --(ε--.

Column 11, line 42, "C8H" should read --$C_8H$--.

UNITED STATES PATENT AND TRADEMARK OFFICE
CERTIFICATE OF CORRECTION

PATENT NO. : 5,026,836
DATED : June 25, 1991
INVENTOR(S) : Roland K. Robins, et al It is certified that error appears in the above-indentified patent and that said Letters Patent is hereby corrected as shown below:

Column 11, line 64, "C8H" should read --$C_8H$--.

Column 11, line 66, "21,80" should read --21.80--.

Column 12, line 14, "cmp" should read --cm--.

Column 12, line 40, "e" should read --$\epsilon$--.

Column 12, line 43, "(t 1 J=3 54 Hz $C_1H$)" should read --(t, 1, J=3.54 Hz, $C_1\underline{H}$)--.

Column 12, line 65, "$C_8$e,uns/H/" should read --$C_8H$--.

Column 13, line 37, "2 KOH" should read --2N KOH--.

Column 14, lines 16-17, "C8e-,uns/H/" should read --$C_8H$--.

Column 14, line 41, "C8e,uns/H/" should read --$C_8H$--.

UNITED STATES PATENT AND TRADEMARK OFFICE
CERTIFICATE OF CORRECTION

PATENT NO. : 5,026,836
DATED : June 25, 1991
INVENTOR(S) : Roland K. Robins, et al It is certified that error appears in the above-indentified patent and that said Letters Patent is hereby corrected as shown below:

Column 14, line 68, "I" should read --1--.

Column 16, line 12, "C8e,uns/H/" should read --$C_8H$--.

Column 16, line 30, "h" should read --1h--.

Column 16, line 43, "C8e,uns/H/" should read --$C_8H$--.

Column 16, line 60, "$C_8$e,uns/H/" should read --$C_8H$--

Column 17, line 15, "IH" should read --1H--.

Column 17, line 21, "pyrazolo-3,4-d1pyrimidine-4-thione" should read --pyrazolo-[3,4-d]pyrimidine-4-thione--.

Column 17, line 30, "were" should read --was--.

Column 17, line 36, "207" should read --2.07--.

Column 17, line 43, "6-Amino-1-$\beta$-D-ribofuranosylpyrazolo[3.4-d1pyrimi-" should read --6-Amino-1-$\beta$-D-ribofuranosylpyrazolo[3,4-d]pyrimi---.

Column 17, line 48, "IN" should read --1N--.

Column 17, line 56, "(5,900)" should read --($\epsilon$5,900)--.

Column 17, line 59, "IH" should read --1H--

UNITED STATES PATENT AND TRADEMARK OFFICE
CERTIFICATE OF CORRECTION

PATENT NO. : 5,026,836
DATED : June 25, 1991
INVENTOR(S) : Roland K. Robins, et al It is certified that error appears in the above-indentified patent and that said Letters Patent is hereby corrected as shown below:

Column 17, line 66, "6-Amino-1-$\beta$-D-ribofuranosylpyrazolo3,4-dlpyrimi-" should read --6-Amino-1-$\beta$-D-ribofuranosylpyrazolo[3,4-d]pyrimi---.

Column 18, line 10, "(66,500)" should read --($\epsilon$6,500)--.

Column 18, line 14, "B.34" should read --8.34--.

Column 18, line 21, "6-Amino-a-$\beta$-D-ribofuranosylpyrazolo[3.4-dlpyrimi-" should read -- 6-Amino-1-$\beta$-D-ribofuranosylpyrazolo[3,4-d]pyrimi- --.

Column 18, line 25, "[3,4d]" should read --[3,4-d]--.

Column 18, line 30, "3 mg" should read --73 mg--.

Column 18, line 43, "6-Amino-1-$\beta$-D-ribofuranosylimidazo[4.5-clpyridine-4-" should read --6-Amino-1-$\beta$-D-ribofuranosylimidazo[4.5-c]pyridine-4---.

Column 18, line 61, "D2O" should read "$D_2O$".

UNITED STATES PATENT AND TRADEMARK OFFICE
CERTIFICATE OF CORRECTION

PATENT NO. : 5,026,836
DATED : June 25, 1991
INVENTOR(S) : Roland K. Robins, et al It is certified that error appears in the above-indentified patent and that said Letters Patent is hereby corrected as shown below:

Column 19, line 3, "6-Amino-1-$\beta$-D-ribofuranosylimidazo4,5-clpyridine-4-" should read -- 6-Amino-1-$\beta$-D-ribofuranosylimidazo[4,5-c]pyridine-4- --

Column 19, line 21, "(s, IH, $C_7\underline{H}$)" should read --(s, 1H, $C_7\underline{H}$)--.

Column 19, line 23, "0.29" should read --20.29--.

Column 19, line 50, "pyrrolo[2,3-dlpyrimidine-4-sulfenamide" should read -- pyrrolo[2,3-d]pyrimidine-4-sulfenamide --.

Column 20, line 3, change "(d, 1, J 3.8 Hz, $C_5\underline{H}$)" should read --(d, 1, J=3.8 Hz, $C_5\underline{H}$)--.

Column 20, line 26, after "pressure" insert --.--.

Column 20, lines 36-37, "$C_8$e-,uns/H/" should read --$C_8H$--.

Column 20, line 39, "5.0I" should read --5.01--.

Column 20, line 58, "(4,400)" should read --($\epsilon$4,400)--.

Column 20, line 59, "4,300)" should read --($\epsilon$4,300)--.

Column 20, line 60, "1, J 5.25 Hz, $C_1\underline{H}$)" should read --1, J=5.25 Hz, $C_1\underline{H}$--.

UNITED STATES PATENT AND TRADEMARK OFFICE
CERTIFICATE OF CORRECTION

PATENT NO. : 5,026,836
DATED : June 25, 1991
INVENTOR(S) : Roland K. Robins, et al It is certified that error appears in the above-indentified patent and that said Letters Patent is hereby corrected as shown below:

Column 20, line 63, "4 49" should read --4.49--.

Column 21, line 19, "(6 6,500)" should read --($\epsilon$6,500)--.

Column 21, line 20, "1H NMR" should read --$^1$H NMR--.

Column 21, line 20, "CH3" should read --$CH_3$--.

Column 21, line 23, "C$_8$e,uns/H/" should read --$C_8H$--.

Column 21, line 49, "3 98" should read --$\delta$ 3.98--.

Column 21, line 51, "C$_8$e,uns/H/" should read --$C_8H$--.

Column 22, line 30, "C$_8$e,uns/H/" should read --$C_8H$--.

Column 22, line 63, "d$_6$) 4.09" should read --d$_6$) $\delta$ 4.09--.

Column 22, line 65, "C8e,uns/H/" should read --$C_8H$--.

Column 22, line 66, "ClO" should read --C10--.

UNITED STATES PATENT AND TRADEMARK OFFICE
CERTIFICATE OF CORRECTION

PATENT NO. : 5,026,836

DATED : June 25, 1991

INVENTOR(S) : Roland K. Robins, et al

Page 8 of 12

It is certified that error appears in the above-indentified patent and that said Letters Patent is hereby corrected as shown below:

Column 23, line 25, "J 4.08" should read --J=4.08--.

Column 23, line 50, "17,300)" should be --($\epsilon$17,300)--.

Column 23, line 61-62, "7-(2-Deoxy-$\beta$-D-erythro-pentofuranosyl)pyrrolo2,3-d1-pyrimidine-4-sulfenamide" should read --7-(2-Deoxy-$\beta$-D-erythro-pentofuranosyl)pyrrolo[2,3-d]-pyrimidine-4-sulfenamide--.

Column 24, line 12, "9,900)" should read --($\epsilon$9,900)--.

Column 24, line 23-24, "7-(2-Deoxy-$\beta$-D-erythro-pentofuranosyl)pyrrolo[2,3-d1-pyrimidine-4-sulfenamide" should read --7-(2-Deoxy-$\beta$-D-erythro-pentofuranosyl)pyrrolo[2,3-d]-pyrimidine-4-sulfenamide--.

Column 24, line 41, "J 6.8 Hz" should be --J=6.8 Hz--.

Column 24, line 44, "C11H14N4O4S" should read --$C_{11}H_{14}N_4O_4S$--.

Column 25, line 11, "1-$\beta$-D-Ribofuranosylpyrazolo3,4-d1pyrimidine-4-sul-" should read --1-$\beta$-D-Ribofuranosylpyrazolo[3,4-d]pyrimidine-4-sul- --.

Column 25, line 58, "7,700)" should read --($\epsilon$7,000)--.

UNITED STATES PATENT AND TRADEMARK OFFICE
CERTIFICATE OF CORRECTION

PATENT NO. : 5,026,836
DATED : June 25, 1991
INVENTOR(S) : Roland K. Robins, et al It is certified that error appears in the above-indentified patent and that said Letters Patent is hereby corrected as shown below:

Column 25, line 59, "$\delta$ 6 2.03-2.13" should read --$\delta$ 2.03-2.13--.

Column 25, line 63, "42,10" should read --42.10--.

Column 41, line 67, "Compound 19 is dissolved i the water" should read --Compound 19 is dissolved in the water--.

Column 43:
Claim 1, lines 3-8, that portion of the figure reading:

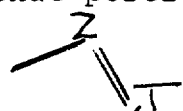

should read:

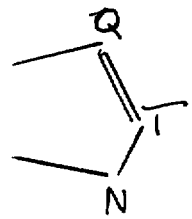

Claim 1, line 18 of claim 1, "O is N" should read --Q is N--;
Claim 1, line 19 of claim 1, "O is C-H" should read --Q is C-H--;

UNITED STATES PATENT AND TRADEMARK OFFICE
CERTIFICATE OF CORRECTION

PATENT NO. : 5,026,836
DATED : June 25, 1991
INVENTOR(S) : Roland K. Robins, et al It is certified that error appears in the above-indentified patent and that said Letters Patent is hereby corrected as shown below:

Column 43:
Claim 1, line 20 of claim 1, "O is C-H" should read --Q is C-H--;
Claim 1, line 21 of claim 1, "O is N" should read --Q is N--.

Column 45:
Claim 18, line 1 of claim 18, "An pharmaceutical composition" should read --A pharmaceutical composition--;

Claim 18, line 23 of claim 18, "O is N" should read --Q is N--;
Claim 18, line 24 of claim 18, "O is C-H" should read --Q is C-H--;
Claim 18, line 25 of claim 18, "O is C-H" should read --Q is C-H--;
Claim 18, line 26 of claim 18, "O is N" should read --Q is N--.

Column 45:
Claim 19, line 4 of claim 19, "G and Z are N" should read --G and Q are N--.

Column 46:
Claim 22, line 1 of claim 22, "An pharmaceutical composition" should read --A pharmaceutical composition-- .

UNITED STATES PATENT AND TRADEMARK OFFICE
CERTIFICATE OF CORRECTION

PATENT NO. : 5,026,836
DATED : June 25, 1991
INVENTOR(S) : Roland K. Robins, et al It is certified that error appears in the above-indentified patent and that said Letters Patent is hereby corrected as shown below: Column 46:

Claim 24, lines 5 - 13 of claim 24, that portion of the figure reading:

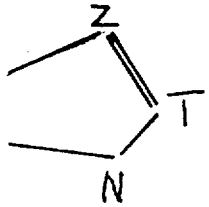   should read:   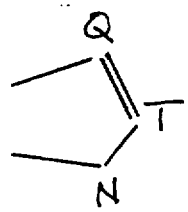

Claim 24, line 25 of claim 24, "W is N" should read --Q is N--;

Claim 24, line 26 of claim 24, "O is C-H" should read --Q is C-H--;

Claim 24, line 27 of claim 24, "O is C-H" should read --Q is C-H--;

Claim 24, line 28 of claim 24, "O is N" should read --Q is N--.

UNITED STATES PATENT AND TRADEMARK OFFICE
CERTIFICATE OF CORRECTION

PATENT NO.    : 5,026,836
DATED         : June 25, 1991
INVENTOR(S)   : Roland K. Robins, et al It is certified that error appears in the above-indentified patent and that said Letters Patent is hereby corrected as shown below:

Claim 24, Column 46, line 28 "O is N" should read --Q is N--.

Signed and Sealed this

Thirty-first Day of May, 1994

Attest:

BRUCE LEHMAN

Attesting Officer           Commissioner of Patents and Trademarks